US008666926B1

(12) United States Patent
Nease et al.

(10) Patent No.: US 8,666,926 B1
(45) Date of Patent: Mar. 4, 2014

(54) METHODS AND SYSTEMS FOR IMPROVING THERAPY ADHERENCE

(75) Inventors: Robert F. Nease, St. Louis, MO (US); David A. Tomala, Chesterfield, MO (US); Seda Follis, St. Louis, MO (US); Tina L. Bauman Butcher, Indianapolis, IN (US)

(73) Assignee: Express Scripts, Inc., St. Louis, MO (US)

( * ) Notice: Subject to any disclaimer, the term of this patent is extended or adjusted under 35 U.S.C. 154(b) by 148 days.

(21) Appl. No.: 13/066,664

(22) Filed: Apr. 19, 2011

Related U.S. Application Data

(60) Provisional application No. 61/325,743, filed on Apr. 19, 2010, provisional application No. 61/474,191, filed on Apr. 11, 2011.

(51) Int. Cl.
*G06F 17/00* (2006.01)
*G06N 5/02* (2006.01)

(52) U.S. Cl.
USPC ................. 706/50; 706/52; 705/2; 705/3

(58) Field of Classification Search
None
See application file for complete search history.

(56) References Cited

U.S. PATENT DOCUMENTS

| | | | |
|---|---|---|---|
| 6,587,829 B1* | 7/2003 | Camarda et al. | 705/3 |
| 7,054,706 B2 | 5/2006 | Kempf et al. | |
| 7,389,211 B2 | 6/2008 | Abu El Ata et al. | |
| 7,533,038 B2 | 5/2009 | Blume et al. | |
| 7,561,158 B2 | 7/2009 | Abe et al. | |
| 7,565,304 B2 | 7/2009 | Casati et al. | |
| 2002/0002473 A1 | 1/2002 | Schrier et al. | |
| 2006/0085230 A1 | 4/2006 | Brill et al. | |
| 2006/0184391 A1 | 8/2006 | Barre et al. | |
| 2008/0109252 A1* | 5/2008 | LaFountain et al. | 705/2 |
| 2010/0205008 A1 | 8/2010 | Hua et al. | |
| 2010/0241459 A1 | 9/2010 | Rao | |

* cited by examiner

*Primary Examiner* — Kakali Chaki
*Assistant Examiner* — Luis Sitiriche
(74) *Attorney, Agent, or Firm* — Bryan Cave LLP

(57) ABSTRACT

A system and method for improving adherence to therapy programs, in particular to adherence to medication therapy and/or to healthcare therapy, that includes medication therapy. Methods of the present invention may also be used to improve compliance with and/or adherence to other wellness and/or health care programs. Methods and systems of the invention may include methods of identifying patients who are at risk of non-adherence, non-compliance, or likelihood of cessation with a therapy program, predicting a basis for such noncompliance, and targeting interventions directed to patients who have been identified as likely to be non-compliant, wherein interventions take into consideration the predicted basis for noncompliance.

16 Claims, 25 Drawing Sheets

METHODS AND SYSTEMS FOR IMPROVING THERAPY ADHERENCE

CROSS-REFERENCE TO RELATED APPLICATIONS

This application claims the benefit of United States Provisional Patent Application entitled "Methods for Improving Therapy Adherence", Ser. No. 61/325,743, filed 19 Apr. 2010 and United States Provisional Patent Application entitled "Methods for Improving Therapy Adherence", Ser. No. 61/474,191, filed 11 Apr. 2011, the entire contents of the applications are herein incorporated by reference.

FIELD

This application relates generally to medical therapy adherence and, more particularly, to predicting drug therapy adherence and improving drug therapy adherence.

BACKGROUND

There is a continuing challenge to reduce the costs of health care. One of the biggest drivers of this cost is prescription drug coverage. Increased prescription drug adherence could lead to reduced waste in medical costs and productivity. Research has shown that non-adherence can have a profound effect on not only an individual's health, but on the health care system as a whole, costing up to $100 billion annually.

Additionally, 33% to 69% of all medication-related hospital admissions in the United States are due "to poor medication adherence, and non-adherence contributes to annual indirect costs exceeding $1.5 billion in lost earning and $50 billion in lost productivity. A November 2009 employer survey from the National Pharmaceutical Council found that medication compliance was a top priority for employers, who are looking to their pharmacy benefit managers (PBM) for solutions.

BRIEF DESCRIPTION OF THE DRAWINGS

FIGS. 14A, 14B-1, and 14B-2 are a block diagram of the TAPO (Therapy Adherence Proactive Outreach) Experience flow for an experienced member, according to an example embodiment;

DETAILED DESCRIPTION

Figure 1:
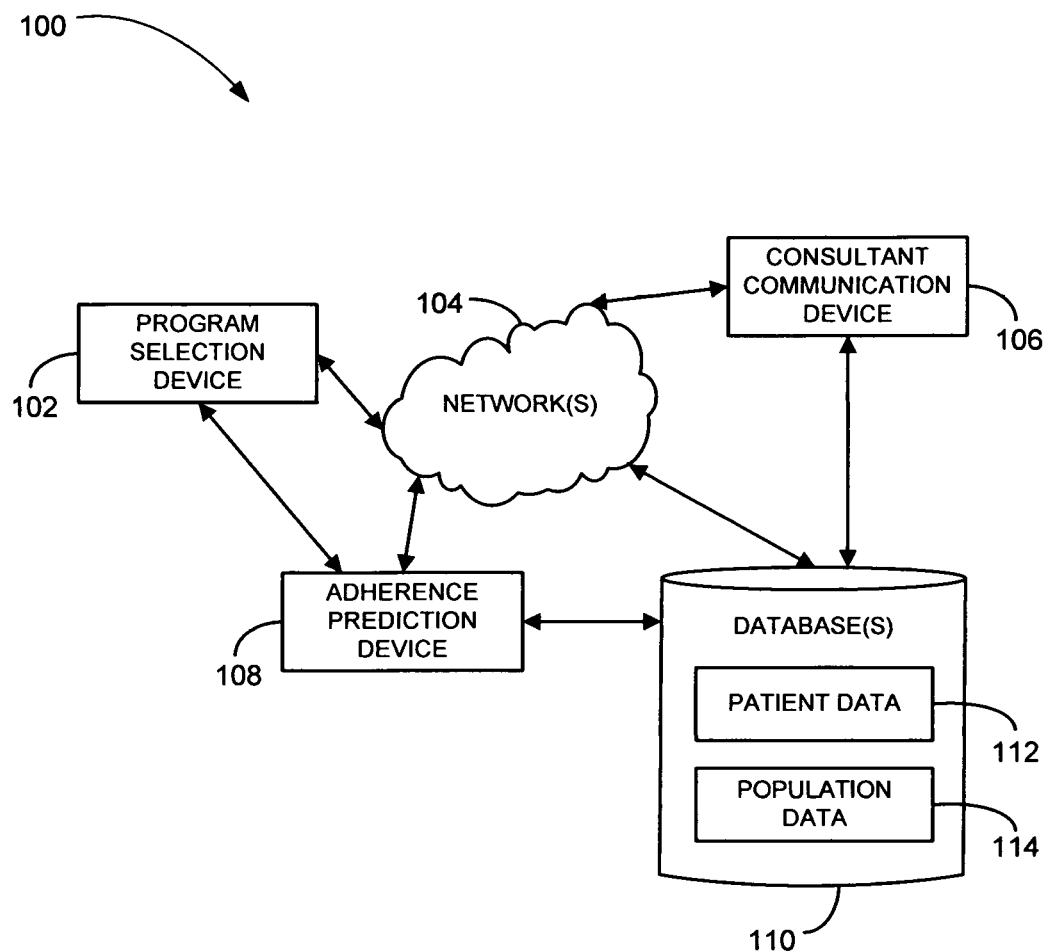
FIG. 1 is a block diagram of an example system, according to an example embodiment.

Example methods and systems for improving therapy adherence are described. In the following description, for purposes of explanation, numerous specific details are set forth in order to provide a thorough understanding of example embodiments. It will be evident, however, to one of ordinary skill in the art that embodiments of the invention may be practiced without these specific details.

The methods and systems are directed to improving adherence to therapy programs; in particular, to adherence to medication therapy and/or to healthcare therapy that includes medication therapy. The methods and systems may also be used to improve compliance with and/or adherence to other wellness and/or health care programs.

In general, the methods and systems may include methods of identifying patients who are at risk of non-adherence, non-compliance, or likelihood of cessation with a therapy program, predicting a basis for such noncompliance, and targeting interventions directed to patients who have been identified as likely to be non-compliant, wherein interventions take into consideration the predicted basis for noncompliance. In addition, the methods and systems include methods of creating benefit plans that promote adherence to therapy programs comprising identifying members who are at risk of non-compliance with a therapy program, predicting a basis for such non-compliance, and structuring the benefit plan or program offering for such member to increase the likelihood of compliance and/or adherence and to reduce the likelihood of cessation of the therapy.

Factors and various demographics have been identified as well as patient's historical compliance that can be used to predict whether a particular patient is likely to be compliant with a therapy program; such factors can be included in a predictive tool, wherein the predictive tool can be used to predict the likelihood of therapy compliance.

The following are examples of compliance indicators that may be associated with therapy adherence:

Older age
Greater income
Higher disease severity
Greater number of medications
Symptomatic disease
Being partnered
Partner adherent to maintenance medications Other factors that affect lack of adherence may include increasing the cost (or copayment) of medications may result in decrease of their use. However, the reverse may be true to a far lesser extent: decreasing the cost/copayment for medications has a very modest effect on increasing adherence.

The methods and systems may also include a method of improving therapy adherence such as promoting the home delivery channel (e.g., mail-order pharmacy). For example, patients that are less likely to be adherent to a therapy program are identified and such patients are targeted for promotion of home delivery of pharmaceuticals.

The methods and systems may be used to create benefit plans in which plans for those members identified as less likely to be compliant with therapy are structured to promote home delivery of pharmaceuticals. The methods and systems may also assess and detect a primary non-adherence cause for a patient identified as likely to be non-compliant; of course, identifying a patient as likely to be non-compliant can occur simultaneously with identification of a primary non-adherence cause.

In general, a patient may be given a prescription drug as part of a therapy for a particular medical or health condition. In participating in drug therapy, the patient taking the prescription drug will generally be considered adherent when the patient takes the drug as prescribed. When the patient does not take the prescription drug, or does not take the prescription drug as prescribed (e.g., the number of times per day and/or at the appropriate times per day), the patient may generally be deemed to not be adherent. The methods and systems may be used to address failures in adherence to drug therapy and may be used to increase the likelihood that a patient will adhere to his or her drug therapy.

Programs to increase adherence to drug therapy may include interventions. Examples of interventions include, by way of example, letters or other communications; use of home delivery and/or specialty pharmacy to fill and/or refill prescriptions; devices adapted to remind a patient to take medication, notify a patient if a dose has been missed, and/or remind a patient that a refill is due; and/or changes to a patient's cost for the drug therapy, e.g., a reduction in co-pay.

In one embodiment, a potentially non-compliant patient is further identified as associated with one of three primary non-adherence causes. Specifically:

Sporadic forgetters are those patients who have a positive perceived value of therapy and are not intentional in the adherence behavior. They periodically neglect to take their medications, and as a result are not adherent.

Active decliners do not—for a variety of reasons—place a positive value on their therapy. This could be because they believe the medication isn't effective, are experiencing side effects, don't like being "prescribed for," or don't believe the medication offers sufficient benefit relative to the cost. As a result, they actively choose not to take their medications as prescribed.

Refill procrastinators do a good job taking their medications as long as they have pills on hand. As their supply dwindles, however, they put off getting a refill. As a result, they may experience a gap in care. This behavior is less intentional than active decliners and does not reflect a negative view of therapy itself.

Having identified a patient as at risk of non-adherence and/or having identified such patient's primary non-adherence cause according to one embodiment, such methods may further include targeting such patient for intervention, wherein such intervention takes into consideration such patient's primary non-adherence cause. Interventions may include, by way of example:

letters combining authority (e.g., signed by chief medical officer and/or a physician) and loss aversion (pointing out risks of non-adherence rather than benefits of adherence);
reduction of copayments;
reminder systems (particularly effective for sporadic forgetters);
auto-refill programs (particularly effective for refill procrastinators);
financial assistance (particularly effective for active decliners);
discussion with a clinician (particularly effective for active decliners).

The predictive modeling techniques of the present invention may be uniquely applied to pharmaceutical data. For example, the methods and systems may be applied to data available to pharmacy benefit managers (PBMs). In one embodiment, a patient identified as likely to be non-adherent can be provided with a container for his or her medication that incorporates reminding techniques. Products that are designed to provide patient reminders can be targeted to the particular primary nonadherence cause of such patient. On the other hand, data gathered from such products can be used to predict a patient's primary non-adherence cause and identify other interventions that may be appropriate for such patient, based on such patient's predicted (or identified) primary nonadherence cause.

A product manufactured under the name GLOWCAP by Vitality, Inc. and/or data available from use of such product, may be used. In one embodiment, a container (e.g., a prescription bottle capped with a GLOWCAP) may include a mechanism to determine whether it has been opened. In such instance, the medication may be presumed to have been taken.

The GLOWCAP device for example, which also includes a wireless transmitter, will light when it is time for a dose of medicine. After a period of time (an hour, for example), the cap will emit a sound. The sound may vary, e.g., in tempo, complexity, and or volume as additional time passes. The particular change and/or timing of changes may be targeted based on a particular patient's identified and/or predicted primary non-adherence cause. Such a cap may be further programmed to send a message of some sort (e.g., email, text, phone call, and/or letter) to the patient, a patient advocate (e.g., a family member), and/or the patient's physician. Again, the content and/or recipient of such message may be targeted based on the patient's primly non-adherence cause.

For example, a message to a patient's physician may be most effective for an active decliner whereas a text message to the patient may be most effective for a sporadic forgetter. Others may include type of pre-commitment, benchmarking of adherence against other patients at an aggregated level, entrance into lotteries for patients who take their medications each day, and other methods. By way of further example, patients identified as at higher risk of non-adherence might escalate more quickly through the flashing, beeping and phone call reminders.

In one embodiment, patients more likely to benefit from an intervention may be identified and/or targeted based on a health condition. Such health condition may be known (e.g., affirmatively included in patent data available to a PBM or other party) or predicted (e.g., based on available data regarding prior prescriptions, treatments, and the like).

For example, patients requiring therapy for depression, mental health issues, asthma, diabetes, hypertension, lipids, osteoporosis, multiple sclerosis, rheumatoid arthritis, and/or hepatitis C may be particularly benefit by use of the methods and systems for improving therapy adherence. The applications of predictive modeling of the methods and systems may also be used to identify a window of time in which intervention is most likely to be effective. For example, a sporadic forgetter may benefit from periodic reminders whereas a refill procrastinator may benefit most from an intervention that occurs at or near the expiration of an existing prescription fill. Early interventions may be most effective for an active decliner.

In some embodiments, enrollment of patients identified as likely to be nonadherent as identified via predictive modeling in specialty pharmacy program may lead to greater therapy adherence. By targeting specialty pharmacy programs for those patients deemed more likely to be non-compliant and/or non-adherent based on behavioral characteristics of those patients, the resources of the specialty pharmacy can be more effectively and efficiently used. Plan benefits can be designed to incorporate specialty pharmacy for such a targeted group of members.

Data used to predict a patient's likelihood of therapy adherence and/or a patient's primary non-adherence cause may include data points related to:

Demographics, e.g., age, gender, whether a partner is present, level of education, level of income (estimated or actual), place of residence, information about the prescribing physician, consumer behavior segmentation attributes such as NE66 segment, life stage grouping, prescription history rescription history, e.g., whether the patient is a participant in concurrent therapy;

Past behavior, e.g., whether the patient has been compliant on other medications, prior average compliance ratio for all "for life drugs";

Other prescription data, e.g., the particular therapy class at issue, the patient's copay, whether the patient participates in home delivery.

Thus, in one embodiment, predictive modeling techniques are applied to data points such as those listed above to: (1) rate a particular patient's risk of non-adherence; (2) prioritize outreach based on predicted risk and refill delay; (3) diagnose adherence problem (e.g., active decline; sporadic forgetter, or refill procrastinator); and (4) intervene as appropriate at member (patient) level.

The predictive modeling techniques may include variable clustering. For example, the SAS procedure VARLCUS with centroid option may be used to cluster variables.

General claims data is unlikely to distinguish among the adherence problems (or categories of non-adherent members). The predictive modeling of the methods and systems may allow classifications not otherwise possible and may promote better and more targeted interventions.

Methods of the present invention can be used to predict patients who are at risk of being non-adherent before they have a gap in a prescription refill and/or care. MPR (medication possession ratio) is a measure that captures a gap in therapy and can be used to measure adherence. Unlike a late to fill measure, MPR is able to detect a gap in care over a period of time. Often, late to fill measures are inaccurate because members may be keeping an extra supply on hand to ensure they don't run out and appear late to fill. MPR is basically a measure that determines if a member has an adequate amount of medication on hand to adequately treat his or her condition.

MPR is generally considered as a day supply of medication within a set measurement period divided by the number of days in the measurement period. According to one embodiment, outreaches are prioritized based on a combination of MPR and refill gap days. Patients considered at highest risk of being non-adherent will receive an outreach much sooner (based on length of refill gap) that patients with a low risk of being non-adherent. By way of example, an outreach may be a diagnostic call that results in a tailored intervention based on the reason for the refill gap.

In some embodiments, three main challenges for interventions that seek to improve adherence. First, the root causes of non-adherence are many, which means no single intervention will solve the adherence problem for a large group of patients. Second, it takes several months of claims data to reliably identify non-adherent patients. This means non-adherent patients are identified after the fact. Finally, the claims data don't provide the level of detail needed to determine the root cause of non-adherence at the patient level. This makes it very difficult to know which intervention is most needed for individual patients. Methods and systems may be applied to address some or all of the three challenges.

Furthermore, methods and systems may eliminate unnecessary costs and member disruption as only patients considered at high risk of not self correcting will receive an outreach. Second, tailored interventions may be offered, versus a one-size-fits-all solution. Finally, by predicting which patients are at elevated risk in advance, methods and systems may promote proactive action rather than reactive action to therapy adherence problems.

Enrolling in a mail order pharmaceutical benefit program, e.g., a program in which prescriptions are fulfilled and medications are delivered to a patient via mail or similar mechanism may provide significant benefits. Costs are typically lower, where "costs" may refer to the cost to the patient, the cost to a health care plan sponsor (such as an employer, a managed care organization, a third party administrator, a purchasing coalition, or a labor union), and/or the cost to other parties involved in the distribution and/or payment chain.

Additionally a mail order program may enhance patient health by, for example, promoting and/or encouraging compliance with a treatment regimen. A method that promotes home delivery and that also provides for automated and/or default refills and/or renewal prescriptions may make it more likely that a patient will obtain and administer a prescribed drug for the duration of the prescription period. Not only does such a method promote the health of the particular patient, it may also promote public health, particularly if the patient is suffering from a transmissible illness.

A prescription benefit plan will often offer a patient a choice between filling a prescription (particularly a prescription for so-called "maintenance" medication and/or another medication in which a fill and/or refill is less time sensitive) at a retail site or via mail order.

In some embodiments, the methods and systems may be used to promote home delivery in which a patient is required to make an "active decision"—specifically, that requires a patient to affirmatively select between retail fills (or refills) and home delivery fills. Even when no penalty is imposed for selecting retail fill over mail order fill for maintenance (or similar) medications (other than the consequence of not receiving the benefits of mail order), participation in mail order may be significantly increased.

In one embodiment, the following elements may be included:
Pre-implementation
Rapid Response
Retail Intervention Pre-implementation may include one or more communications with members and/or patients via, e.g., mail, telephone, email, facsimile, and/or other electronic and/or personal contact method to discuss home delivery and its benefits. Pre-implementation may also include communications about the "active decision" element.

In general, "pre-implementation" refers to communications that, ideally, occur relatively early during the process of implementing a method of the invention. For example, pre-implementation may occur when a new prescription benefit plan is offered and/or at a period at or near renewal of a health plan. "Rapid response" is similar to pre-implementation and includes similar communications, but refers to communications triggered by circumstances that occur outside of the start-up phase of a new plan, a new enrollment period, and the like. For example, "rapid response" may be appropriate when a new employee is hired and/or begins to participate in a prescription benefit program. "Rapid response" may also be appropriate if a member begins taking a new medication, e.g., if a member makes a first fill of a prescription that may be a maintenance medication (based, e.g., on historical prescribing data for such medication).

As noted, a component may include is an active decision element—that in some manner promotes and/or requires an affirmative decision by a participant to select either retail or mail order. In one embodiment, the active decision is promoted and/or required as follows: (1) a set number of allowed retail fills is established, wherein "allowed retail fills" refers to retail fills (in particular, retail fills or maintenance or similar medications) that will be authorized under a prescription benefit plan before the required "active decision" has been made, and (2) when the set number of allowed retail fills has been reached, a retail fill will be initially denied in a "retail intervention." In an embodiment, retail intervention may include: (1) notice to the pharmacist or other employee at the retail site that communication with the PBM is required prior to fulfillment of the prescription; (2) communication between the patient and the PBM is facilitated, preferably at the retail site, via a known communication technique, e.g., telephone; and (3) the patient is informed that the number of allowed retail fills as been reached and is informed of the consequences for continued failure to make an active decision. The number of allowed retail fills can be between 2 and 5; particularly 3. If the number of allowed retails fills is 3, then the $3^{rd}$ maintenance retail fill will be the subject of retail intervention.

In one embodiment, the consequence for failure to make an active decision after the number of allowed retail fills has been reached is that the patient may be required to pay full price for the medication until an active decision has been made. If the retail intervention leads to an active decision, e.g., the patient affirmatively selects either retail fill or mail order fill, the prescription fulfillment process continues either at the retail site or via the mail order program (depending upon the results of the patient's active decision) in accordance with the terms of the prescription benefit plan. For example, the agreed-upon co-payment is made by the patient to receive the prescription.

The method may include communication to the members about the limit on retail fills absent an affirmative decision. For example, as part of re-implementation and/or rapid response, a member may be told of the number of allowed retail fills. In one embodiment, all retail fills (regardless of the type of medication) may be "counted" in determining whether the number of allowed retail fills has been reached. In another embodiment, only fills likely to be appropriate for mail order fulfillment (e.g., maintenance medications) are counted. In yet another embodiment, all retail fills are counted, but retail intervention will occur only with a retail fill likely to be appropriate for mail order. In a still further embodiment, all retail fills are counted and when the number of allowed retail fills has been reached, retail intervention will be implemented regardless of whether the particular prescription is appropriate for mail order. In this embodiment, if a participant selects mail order, then if the particular prescription that prompted retail intervention is not appropriate for mail order, that prescription may be fulfilled at the retail pharmacy, but future prescriptions for mail order appropriate medications will be fulfilled by mail order. In other embodiments, such a prescription may be partially filled, e.g., with a number of units deemed likely to be sufficient until a mail order prescription will arrive at the designated mailing address.

The richness of the input variable set necessitated a method for dimension reduction. Principal component analysis and other methods were considered. However variable clustering may be used as variable clustering may reduce the dimensionality of the model fit and scoring problem, thus simplifying the scoring method and each dimension selected by variable clustering may be used to represent a unique input variable from the original data set. This may ensure that the final scoring method has an intuitive description/explanation. The impact of each individual input may be ascertained directly without the need to interpret weighted combinations for principal components.

Variable clustering, using PROC VARCLUS, reduced input dimensions by approximately 40%.

The SAS procedure VARCLUS with centroid option may be used to cluster variables. Briefly, this procedure collects into clusters variables that are highly correlated (parametrically and non-parametrically via Spearman's and Pearson's correlation coefficients) with each other yet oblique (but not fully orthogonal as in principal component) to other clusters. For each variable in each cluster a ratio (usually referred to as the R-square ratio) is computed as:

$$R \text{ square ratio} = (1 - R^2 \text{ own}) / (1 - R^2 \text{ nearest})$$

Where $R^2$ own is the fraction of the in-cluster variation explained by the variable, and $R^2$ nearest is the fraction of the nearest (not own) cluster variation explained by the variable. Selection may be made from each cluster of a representative that simultaneously represents its own cluster well (by explaining a large share of its own cluster variation) and is as orthogonal to other clusters as possible (by explaining only a small fraction of the variation of the nearest cluster). Such a candidate will have a small R square ratio.

Selection of a candidate may also be weighed in non-tangible factors such as: how intuitive is the candidate? How computationally expensive is it to compute? In general, these factors may be used only as tie-breakers, and for the most part, the variable with the lowest R square ratio was selected as the cluster's representative. Due to the importance (and number) of therapy class variables, separate clustering exercises may be performed for concurrent therapy class and all other input variables.

To focus on the most promising input variables, bivariate screening may be performed on the remaining input variable set. The method may compute Spearman's rank correlation coefficient and Hoeffding's dependence coefficient (D-Statistic) for each remaining input variable against percent compliant. For each input variable, the method may plot the rank order of the Spearman correlation statistic vs. the rank order of the Hoeffding's D statistic. Variables at the upper-right corner of the plot may be eliminated from the input variable list. The rationale for this is that these variables have the least impact on percent compliant.

This plot may also be used to investigate non-monotonic associations. A high Spearman rank, together with a low Hoeffding's D rank, suggests that the relationship between input and percent compliant is not monotonic. These variables may be further explored using empirical logic plots.

Empirical logic plots may be recursively generated for each non-monotonic variable, and bins adjusted at each step, until the plots confirm that any non-linearity had been neutralized. A binned version of the variable may be created using the final bins. The binned variable may be given a b_prefix to differentiate it from its unbinned source. The benchmark model may be selected using PROC REG with SiEPWISE option. Questionable variables may be removed from the model specification, and predictive power and robustness may be reassessed. In cases where the impact of removal was marginal, the offending variables may be permanently removed.

In some embodiments, the method may handle adherence as not one behavior. The method may handle it as two sequential behaviors that are independent of one another. First, the patient will either stay on their medication or not stay on their medication and conditioned on staying on their medication, they will either do a good job or they will do a bad job. By separating those behaviors, that separation of behaviors allows the method to be more robust. The method may include a process where it goes through to look at the disease state and how long the patient has been in therapy, and then there are more particular factors that the method may look at when making the adherence prediction. The weighting that the method uses for those factors may be unique.

In some embodiments, the predictions that the method produces are created by multiplying the likelihood of continuing therapy times the medication possession ratio MPR. MPR, measures the amount of medication someone uses over a reporting period. For example, if there are 100 days in a reporting period and an individual has 100 pills, its 100 divided by 100, the ratio, they're 100% adherent. If the person only obtained 50 pills in 100 days and the person take one a day, they're 50% adherent. In some embodiments, MPR data can be collected by using drug claims.

If that reporting period starts on May 1, and someone got a prescription for 30 pills filled on April 25, the model may only provide credit for the part of the fill, the partial fill that started on May 1. The model may only count the number of pills that are actually in the reporting period in order to avoid the error of only counting the fills that actually occurred within the reporting period. However, taking an arbitrary window of time measurements for MPR may introduce a huge amount of noise. Therefore, the model may also evaluate the patient's behavior.

The model may determine when the person fills and measure the MPR based upon the two points between which they got filled. For example, if the person received a fill on January 1st and the model detects a bunch of fills and the last fill detected for the year is November 30, then the model does not measure that number from January 1st to December $31^{st}$, but only measures that number from January 1st to November 30th so that the measurement window is in accordance with the behavior of the number.

Those are two different metrics may be used to measure adherence. So that multiplication is the score we are talking about and that score is now called the adherence index. On a periodic basis, for example a weekly basis, the method can have a daemon that wakes up, goes to all the patients that are on hypertension, crunches the algorithm, populates that back to the database.

The method may utilize an adherence index rather than using a raw score. The adherence index may be determined from a model. The structure of the model may be determined by examining hundreds of variables in historical data and determining patterns. The model may examine data relating to patient demographics such as age and profession and marital status, Rx history such as concurrent drug treatment and length of time on previous treatments, and past behavior such as cessation of other treatments and/or adherence on other medication treatments. Using the patterns certain probabilities can be determined.

Once the basic models are obtained, real time data may be applied from current patients to further refine the model. There is a probability variable in a cessation model that is indicative of the likelihood of a patient to stop taking medication. The cessation model may be further divided or handled based on disease or therapy type. The cessation model may also be divided by a new patient and an experienced patient.

The models may be used to target high risk patients for outreach. The model may determine likelihood of cessation and if the probability of cessation is sufficiently low the model may determine what is the likelihood of adherence by developing an adherence index. Therefore, the model may have cessation model and an adherence model. Both models may be further divided into sub-models by a new patient model and an experienced patient model, thus resulting in four models.

In general, the adherence index may be determined by factoring the likelihood or probability of adherence developed from demographic data and other data patterns with the patient's MPR. Initially, the model may be built from general population historical demographic data and predicted MPRs. The general population data may also be further segregated by other factors such as by a particular community, or a population within a certain company or a population having a certain category of disease. Individual patient demographics and other individual patient data and individual patient medication possession ratios may be applied against the model to further refine the model. The refinements may be made by evaluating differences between actual and predicted adherence and evaluating related patterns. Once actual data is gathered an actual past MPR can be factored in to further refine the prediction model.

Probabilities regarding cessation and adherence may be developed by evaluating patterns from general historical demographic data and other data such as data for a given disease type or for a type of drug treatment. From these probabilities, a basic model may be developed. The basic model may be refined by correlating individual patient demographics and actual patient behavior with the basic model and updating the model as appropriate. For example, demographic data may include age, income bracket, severity of disease or disease type, number of concurrent medications, symptomatic disease, type of drug treatment, partner status, and partner adherence. The model may capture and statistically evaluate patterns in data that at first glance may appear unrelated to adherence and correlate the pattern to adherence. For example, the model may capture and statistically evaluate lifestyle patterns that have statistical significance to adherence. For example, the model may look at whether a patient consistently gets their prescription refilled at the same location and correlate that to their likelihood of adherence.

The adherence index may also identify the patient as high risk, a likely barrier to adherence can also be determined such as forgetfulness, prescription refill delays or drug cost. From this information, the model may develop an individual patient intervention program, which can include reminder tools, mail order subscriptions, and/or increased dosages requiring the medication be taken less often. The patient intervention program may be decide based on what the model determines would be the most effective program for the given patient, which can be based on historical modeling. Once an intervention program is implemented, the patient may continue to be modeled and data may be collected and related to the patient's adherence and the adherence index can be continuously or periodically updated including the new information being gathered.

Improvements in the adherence index may be tracked and correlated in various ways. For example, the model may determine under what parameters a particular reminder device is most effective or in other words determining the "sweet spot" for a particular intervention program. This continued refinement of the sweet spot may improve the models ability to more efficiently target patients who will be most likely to be impacted by intervention and determine a most effective intervention program for a given patient.

In some embodiments, the use of the methods and systems may promote a more efficient allocation of resources by identifying patients more likely to be responsive to an intervention. In some embodiments, the use of the methods and system may promote a more efficient allocation of resources by identifying patients more likely to be responsive to a particular intervention. The method utilizes a probability predictive tool to target a patient likely not to adhere.

FIG. 1 is a block diagram of an example system 100, according to an example embodiment. The system 100 is an example environment in which therapy adherence of patients may be improved. The system 100 includes a program selection device 102 that may be in communication with a consultant communication device 106 over a network 104.

The program selection device 102 selects a therapy program for a patient that may increase the likelihood of the patient adhering to a drug therapy. In general, drug therapy adherence refers to whether the patient continues treatment or stops treatment of a drug for a particular condition. By way of example, if a patient has a 30% likelihood of discontinuing therapy, he or she has a 70% likelihood of continuing therapy. Other scores (e.g., a scale from 0 to 1) may be used to identify a measured likelihood of continuing or discontinuing therapy.

The program selection device 102 may identify a therapy adherence program for a patient, based on his or her likelihood of therapy adherence. In an example embodiment, a program selection may be a selection of no program or intervention if, e.g., no program has been identified as likely to increase therapy adherence or if the patient is identified as so likely to be adherent that an intervention is unnecessary. The program selection device 102 may also be used to identify those patients and corresponding programs that may be most likely to improve therapy adherence thus allowing resources to be targeted where they are relatively more likely to have a significant impact on therapy adherence.

Therapy programs that may be more likely to be effective in improving therapy adherence of patients with a particular likelihood of therapy adherence may be identified based on a score and/or range of scores.

The network 104 by which the devices 102, 106 communicate may include a Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Other conventional and/or later developed wired and wireless networks may also be used.

Communications with patients before and/or after identified therapy programs have been implemented may be facilitated at the consultant communication device 106. For example, a patient consultant may use the consultant communication device 106 to facilitate communications with a patient to gather data points for patient data 112 stored in a database 110 that may be used to determine the patient's likelihood of therapy adherence. After a therapy program has been identified for a particular patient, the consultant communication device 106 may be used to implement or aid in implementing the therapy program. For example, the consultant communication device 106 may generate communications to a patient, may be used to offer home delivery to a patient (and/or enroll a patient in home delivery), and the like. Patient may also have computing or personal digital assistant devices for receiving messages and other communications to improve adherence. Also special applications can be utilized on computing or personal digital assistant devices for management of medications and reminders.

Examples of patient consultants that may operate the consultant communication device 106 include a nurse, pharmacist, and other health care providers and/or personnel trained to administer and/or implement a therapy adherence program.

The adherence prediction device 108 determines a patient's predicted likelihood of continuing drug therapy and predicted likelihood of complying with drug therapy. Compliance with drug therapy refers to how well a patient complies with his or her therapy, assuming it continues. Medication possession ratio (MPR) may be used to measure a patient's compliance.

Very generally, if a patient possesses a total of a 30 day supply of medication over a 45 day period, this indicates a failure to fully comply with the drug therapy. In one example embodiment, a lower MPR score indicates relatively poor compliance compared to a relatively high score indicating good compliance. Other compliance scores may be used. In an example embodiment, a modified MPR that measures MPR based on actual dates of fill is used. In an example embodiment, an MPR that measures MPR based on a predetermined or selected period of time is used. Predicted MPR can be used to measure, score, or otherwise identify a predicted likelihood of therapy compliance. In some example embodiments, a patient's past MPR when available may be used in connection with predicting the patient's future MPR.

Adherence, as identified via an adherence prediction device 108, is based on a combination of a patient's likelihood of continuing therapy and a patient's likelihood of complying with therapy.

In one example embodiment, a separate subsystem is used based on whether a patient is new to therapy (naive) or continuing therapy (experienced). In another example embodiment, the same subsystem is provided for both naive and experienced patients.

In one example embodiment, a separate subsystem is provided based on the patient's disease state and/or drug therapy. For example, one subsystem may be provided for a patient with hypertension, another subsystem may be provided for a patient with diabetes, and still another subsystem may be provided for a patient with lipid disease. In one example embodiment, the subsystem is not dependent upon the patient's disease state or drug therapy. In an example embodiment in which separate subsystems are provided for both disease states and naive and experience patients, then the adherence prediction device 108 may predict adherence for patients with hypertension, diabetes, and lipid disease may include a naive hypertension subsystem, an experienced hypertension subsystem, a naive diabetes subsystem, an experienced diabetes subsystem, a naive lipid disease subsystem, and an experienced lipid disease subsystem.

Examples of the program selection device 102, the consultant communication device 106, and the adherence prediction device 108 include a gaming unit, a mobile phone, a personal digital assistant (PDA), a display device, a generic or specialized computing system, or the like. Other devices may also be used. The program selection device 102, the consultant communication device 106, and the adherence prediction device 108 may each use the same type of device, or may use different types of devices. Furthermore, while the system 100 in FIG. 1 is shown to include single devices 102, 106, 108, multiple devices may be used.

In some embodiments, the program selection device 102, the consultant communication device 106, and the adherence prediction device 108 are combined into a single server, while in other embodiments, the program selection device 102, the consultant communication device 106, and the adherence prediction device 108 operate on separate servers.

The program selection device 102, the consultant communication device 106, and the adherence prediction device 108 may be in communication with a database 110. The database 110 may store patient data 112 and population data 114. The patient data 112 may include patient data received by the consultant communication device 106. The patient data 112 may include patient demographics data, patient prescription history data, and/or patient past prescription behavior data. The patient data 112 may be obtained by a patient consultant, from prescription claim histories, health plan information, and the like. The patient past prescription data may include information that identifies the patient, as to a particular drug therapy, as new (naive) or experienced.

The population data 114 may include population demographics data, population prescription history data, and/or population past prescription behavior data. The population may include a set of individuals who have participated in and/or who have been prescribed one or more drug therapies and/or who are identified as having a particular disease or condition. Other populations may be used such as populations in communities or populations at certain companies of populations meeting certain demographic criteria.

Population demographics data generally includes information about one or more demographic characteristics of a population such as age, gender, income or income range, race, place of residence, employment, and other demographic characteristics. Population prescription history data generally includes information about one or more prescription history characteristics, such as information about concurrent therapies. Population past prescription behavior data generally includes information about one or more past prescription behavior characteristics, such as selection of brand or generic drugs, use of retail or home delivery, adherence to other drug therapies, and the like.

The patient data 112 may be similar to the population data 114 but includes information about the characteristics that is specific to the patient for whom a therapy adherence program may be identified and/or implemented.

Figure 2:
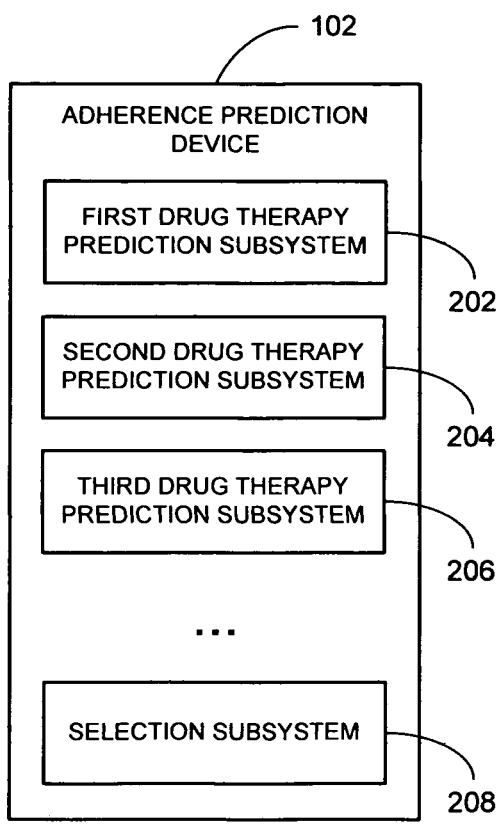
FIG. 2 illustrates an example adherence prediction device that may be deployed in the system of FIG. 1, according to an example embodiment.

FIG. 2 illustrates the adherence prediction device 108, according to an example embodiment. The adherence prediction device 108 includes one or more subsystem employed to predict adherence for each of a set of conditions and/or drug therapy. The adherence prediction device 108 with the subsystems may be deployed in the system 100, or may be deployed in another system.

The adherence prediction device 108 as shown in FIG. 2 includes a first drug therapy prediction subsystem 202, a second drug therapy prediction subsystem 204, a third drug therapy prediction subsystem 206, and a selection subsystem. More or less subsystems may be used.

By way of example, the first drug therapy prediction subsystem 202 may be used to predict adherence for hypertension patients, the second drug therapy prediction subsystem 204 may be used to predict adherence for diabetes patients, and the third drug therapy prediction subsystem 206 may be used to predict adherence for patients with lipid disease. In another example embodiment, a separate prediction subsystem is deployed for patients who are new to a particular drug therapy and for those who are experienced with the drug therapy. The selection subsystem 208 may be used to identify the particular drug therapy prediction subsystem to be deployed in predicting a particular patient's likelihood of compliance.

Figure 3:
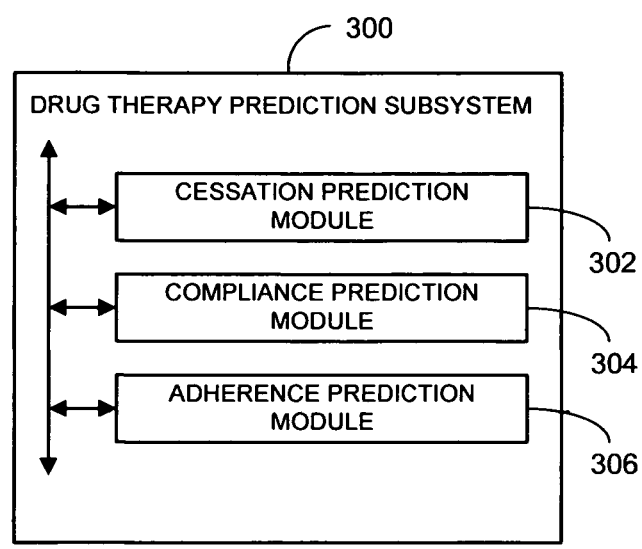
FIG. 3 illustrates an example drug therapy prediction subsystem that may be deployed in the adherence prediction device of FIG. 2, according to an example embodiment.

FIG. 3 illustrates a drug therapy prediction subsystem 300, according to an example embodiment. The drug therapy prediction subsystem 300 may be deployed as a drug prediction subsystem of the prediction subsystems 202-206 in the adherence prediction device 108 of the system 100, or may otherwise be deployed in another system.

The drug therapy prediction subsystem 300 may include a cessation prediction module 302, a compliance prediction module 304, and/or an adherence prediction module 306. Other modules may also be included. In some embodiments, the modules of the drug therapy prediction subsystem 300 may be distributed so that some of the modules are deployed in the adherence prediction device 108 and some modules are deployed in the program selection device 102 and/or the consultant communication device 106. In one embodiment, the modules are deployed in memory and executed by a processor coupled to the memory.

The cessation prediction module 302 predicts the likelihood that a patient discontinues a particular drug therapy. The compliance prediction subsystem 304 predicts the likelihood that a patient complies with a particular drug therapy. The adherence prediction subsystem 306 predicts the likelihood of the adherence of the patient.

Figure 4:
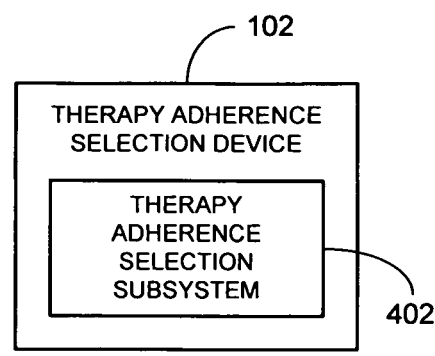
FIG. 4 illustrates an example program selection device that may be deployed in the system of FIG. 1, according to an example embodiment.

FIG. 4 illustrates the program selection device 102, according to an example embodiment. The program selection device 102 includes a program selection subsystem 402. The program selection subsystem 402 identifies a therapy program likely to increase a patient's therapy adherence based on the patient's predicted therapy adherence. For example, communications (e.g., letters or e-mails) have been identified as likely to increase adherence of a patient who is moderately likely to adhere to therapy and devices (e.g., GLOWCAP devices or DOSE-ALERT devices) have been identified as likely to increase adherence of a patient who is less likely to be adherent. Accordingly, if a patient's likelihood of adherence falls within the range for which communications have been identified as a likely successful program, a communication program is identified for that patient by the program selection subsystem 402. The program selection device 102 with the program selection subsystem 402 may be deployed in the system 100, or may be deployed in another system.

Figure 5:
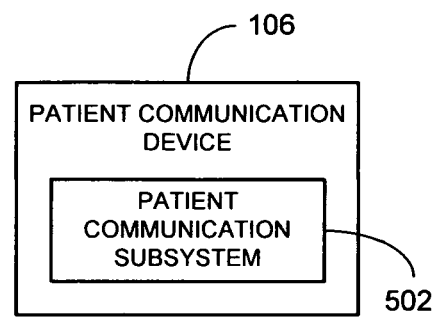
FIG. 5 illustrates an example consultant communication device that may be deployed in the system of FIG. 1, according to an example embodiment.

FIG. 5 illustrates the consultant communication device 106, according to an example embodiment. The consultant communication device 106 includes a patient communication subsystem 502. The consultant communication device 106 with the patient communication subsystem 502 may be deployed in the system 100, or may be deployed in another system.

Figure 6:
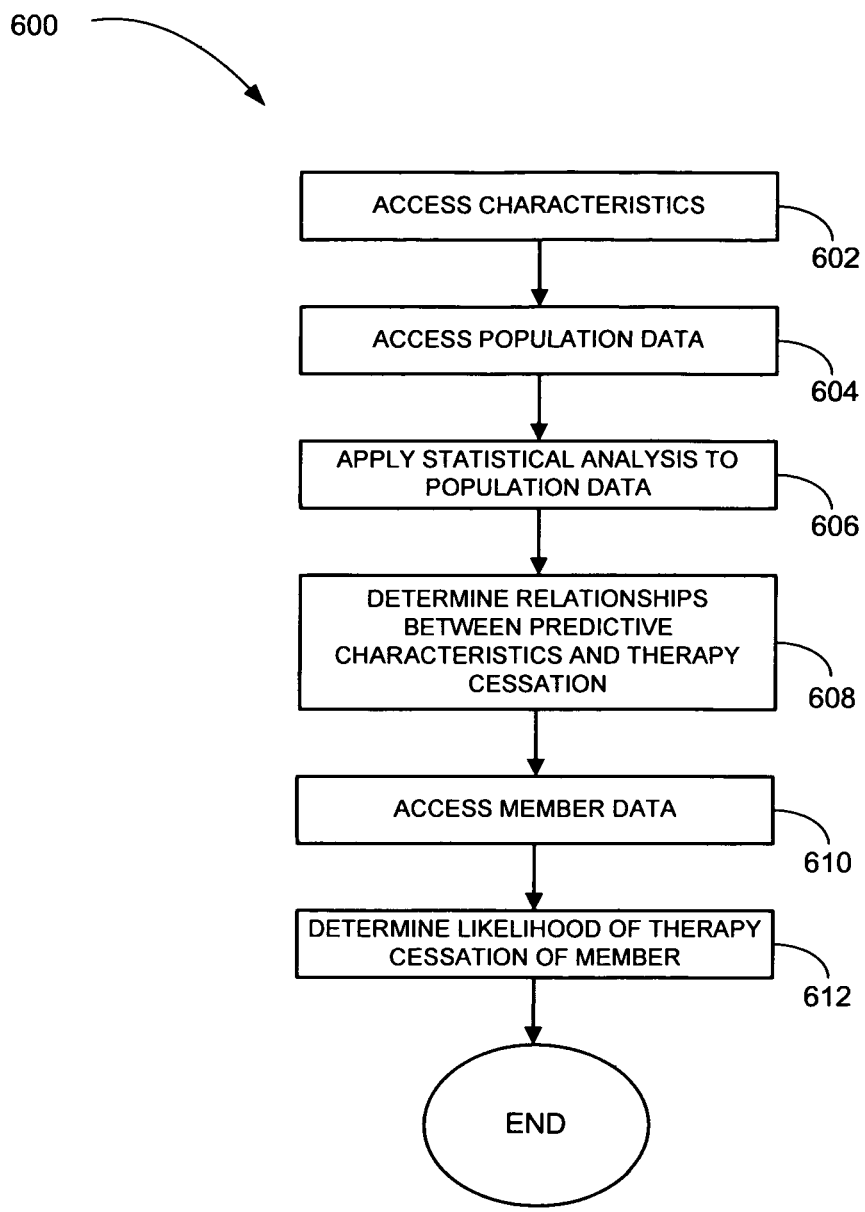
FIG. 6 is a block diagram of a flowchart illustrating a method of predicting likelihood of cessation of therapy, according to an example embodiment.

FIG. 6 illustrates a method 600 of predicting likelihood of cessation of therapy, according to an example embodiment. The method 600 may be performed by the adherence prediction device 108, or may be otherwise performed. In some embodiments, the method 600 may be performed by the cessation prediction module 302 (see FIG. 3).

At block 602, a set of characteristics that may be predictive of therapy cessation is accessed. Population data is accessed at block 604. At block 606, statistical analysis techniques are applied to the population data to identify predictive characteristics. In some embodiments, the identified characteristics are characteristics that are predictive of therapy cessation. At block 608, a determination is made of the relationships between the predictive characteristics and therapy cessation. In some embodiments, the resulting determination is a co-variance. In some embodiments, statistical regression analysis techniques may be used to determine the relationships.

The operations performed at blocks 602-608 need not be carried out in each instance in which a therapy adherence program is identified for a particular patient or in which the likelihood of therapy cessation is determined. In an example embodiment, the results of the operations, once performed, are retained for future use. In an example embodiment, the operations are periodically repeated to identify new predictive characteristics and/or new relationships. At block 610, the patient data 112 for each predictive characteristic is accessed. At block 612, the patient's likelihood of therapy cessation is determined based on the relationships between the predictive characteristics and likelihood of therapy cessation.

Figure 7:
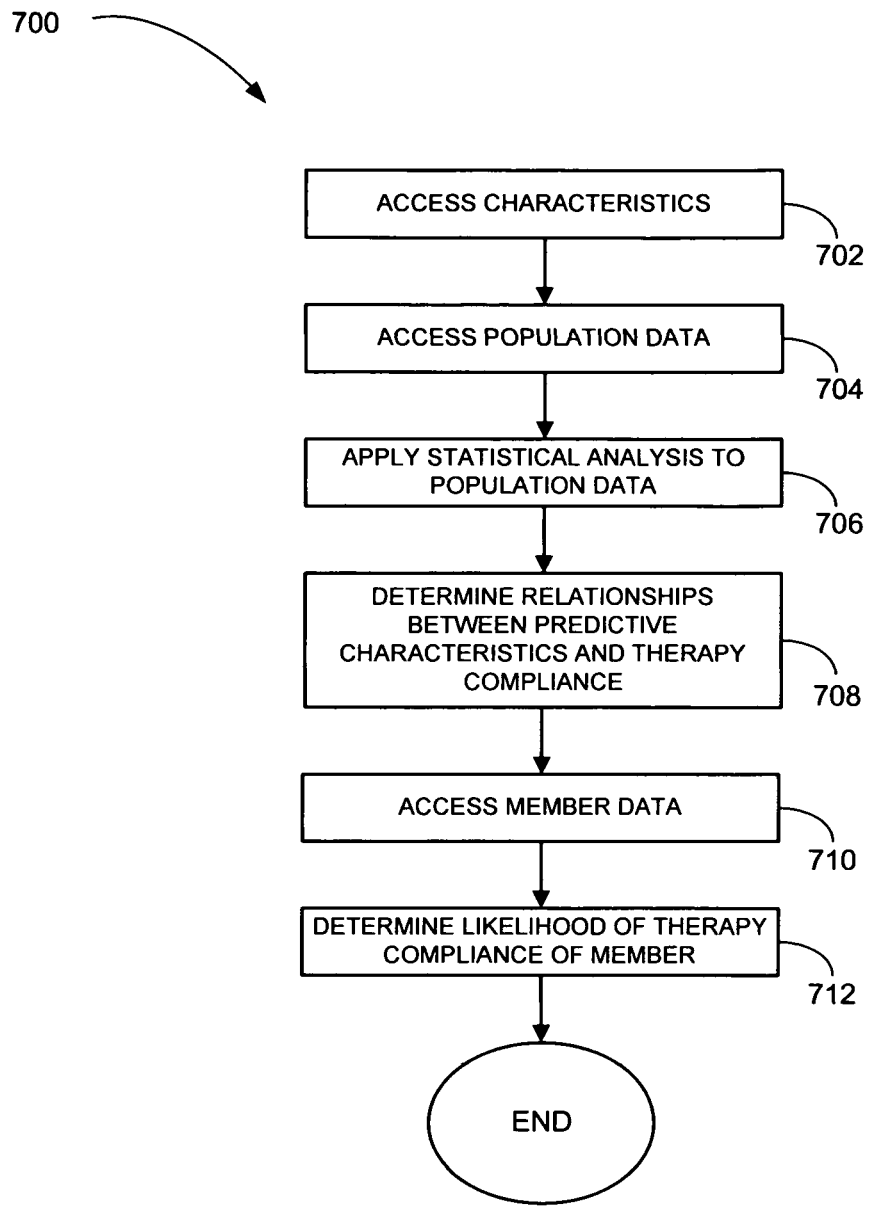
FIG. 7 is a block diagram of a flowchart illustrating a method of predicting therapy compliance, according to an example embodiment.

FIG. 7 illustrates a method 700 for predicting therapy compliance, according to an example embodiment. The method 700 may be performed by the adherence prediction device 108, or may be otherwise performed. In some embodiments, the method 700 may be performed by the compliance prediction module 304 (see FIG. 3). At block 702, a set of characteristics that may be predictive of therapy compliance is accessed. Population data is accessed at block 704.

At block 706, statistical analysis techniques are applied to the population data to identify predictive characteristics. In some embodiments, the identified characteristics are characteristics that are predictive of therapy compliance. At block 708, a determination is made of the relationships between the predictive characteristics and therapy compliance. In some embodiments, the resulting determination is a co-variance. In some embodiments, statistical regression analysis techniques may be used to determine the relationships.

The operations performed at blocks 702-708 need not be carried out in each instance in which a therapy adherence program is identified for a particular patient or in which the likelihood of therapy compliance is determined. In an example embodiment, the results of the operations, once performed, are retained for future use. In an example embodiment, the operations are periodically repeated to identify new predictive characteristics and/or new relationships. At block 710, the patient data 112 for each predictive characteristic is obtained. At block 712, the patient's likelihood of therapy compliance is determined based on the relationships between the predictive characteristics and likelihood of therapy compliance.

Figure 8:
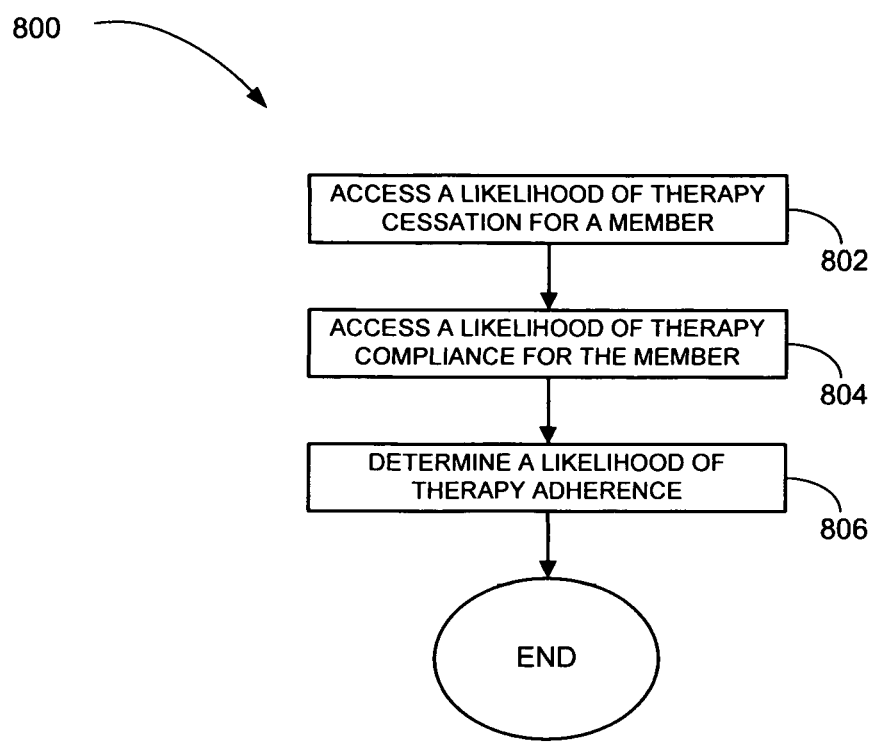
FIG. 8 is a block diagram of a flowchart illustrating a method of predicting therapy adherence, according to an example embodiment.

FIG. 8 illustrates a method 800 for predicting therapy adherence, according to an example embodiment. The method 800 may be performed by the adherence prediction device 108, or may be otherwise performed. In some embodiments, the method 800 may be performed by the adherence prediction module 306 (see FIG. 3). A patient's likelihood of therapy cessation is accessed at block 802. A patient's likelihood of therapy compliance is accessed at block 804.

A patient's likelihood (or probability) of therapy adherence is determined at block 806 based on the patient's likelihood of therapy cessation and therapy compliance. For example, the patient's likelihood of therapy cessation and therapy compliance may be multiplied, added, or otherwise combined. The patient's likelihood of therapy cessation and/or therapy compliance may be weighted in the calculation.

Figure 9:
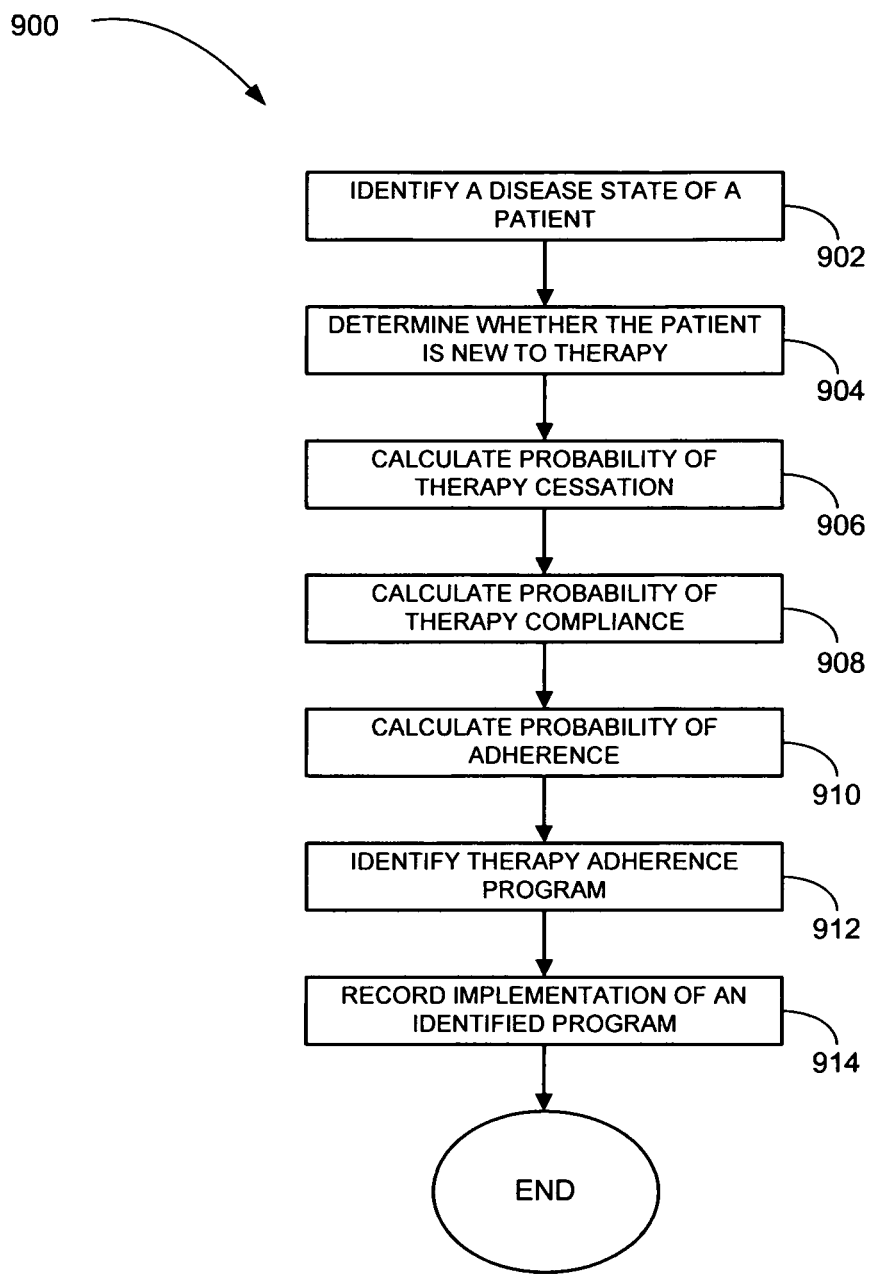
FIG. 9 is a block diagram of a flowchart illustrating a method for therapy program implementation, according to an example embodiment.

FIG. 9 illustrates a method 900 for therapy program implementation, according to an example embodiment. The method 900 may be used to improve a patient's likelihood of therapy adherence. The method 900 may be performed by the adherence prediction device 108, partially by the adherence prediction device 108 and partially by the program selection device 102 and/or the consultant communication device 106, or may be otherwise performed.

A patient's disease state is identified at block 902. A patient's disease state may be identified based on the patient data 112, through the consultant communication device 106, or may be otherwise identified. Examples of the patient's disease state may include hypertension, diabetes, and lipid disease. Other disease states may also be used. The probability of therapy cessation is calculated at block 906. The probability of therapy compliance is calculated at block 908. The probability of adherence of the patient is calculated at block 910. A therapy adherence program (e.g., an intervention) is identified at block 910 based on the patient's probability of adherence.

An implementation of an identified program may be recorded at block 912. The therapy adherence program may be implemented through the consultant communication device 106, or may be otherwise implemented.

Figure 10:
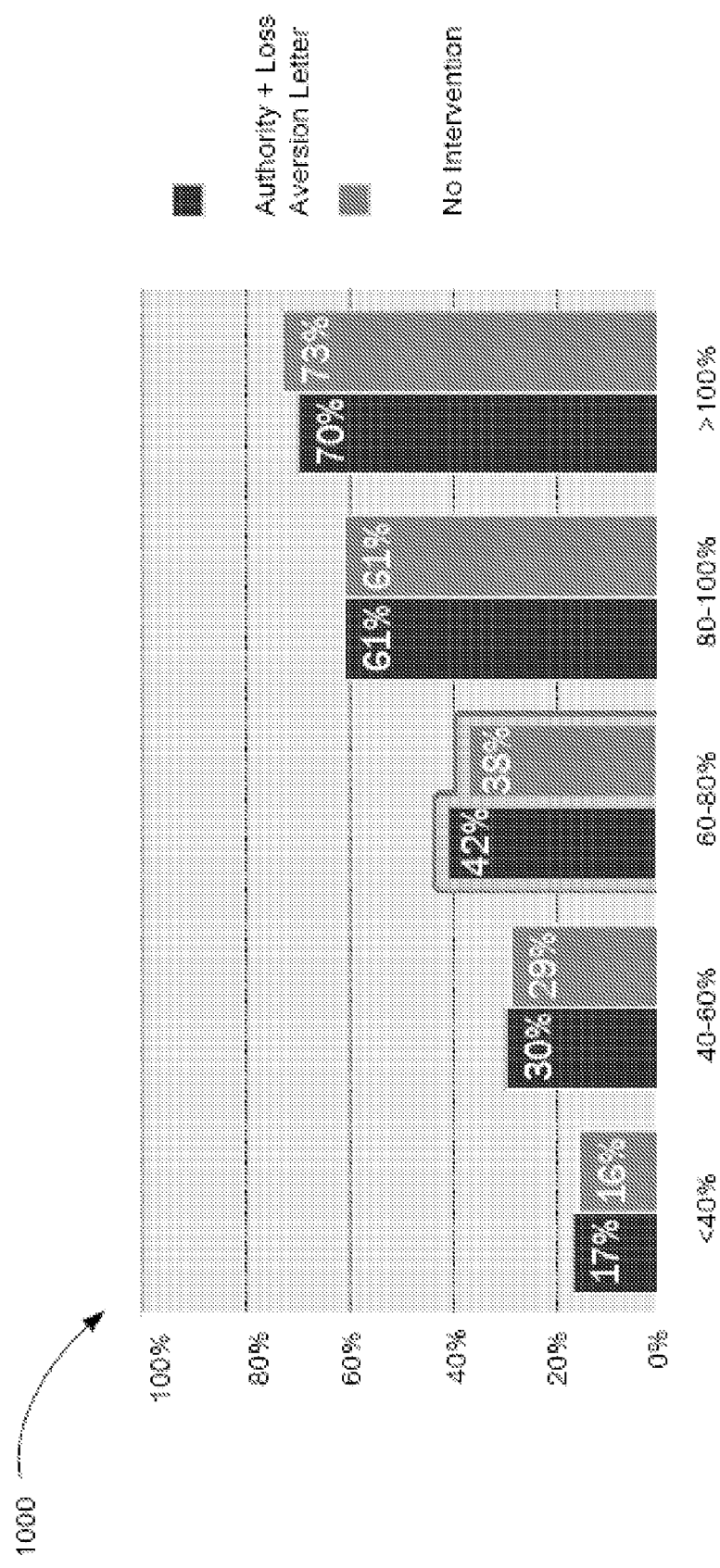
FIGS. 10 and 11 are charts, according to example embodiments.

FIG. 10 is an example chart 1000, according to an example embodiment. The chart 1000 indicates an example study of a population. A certain portion of the population having a low adherence rate may be targeted.

Figure 11:
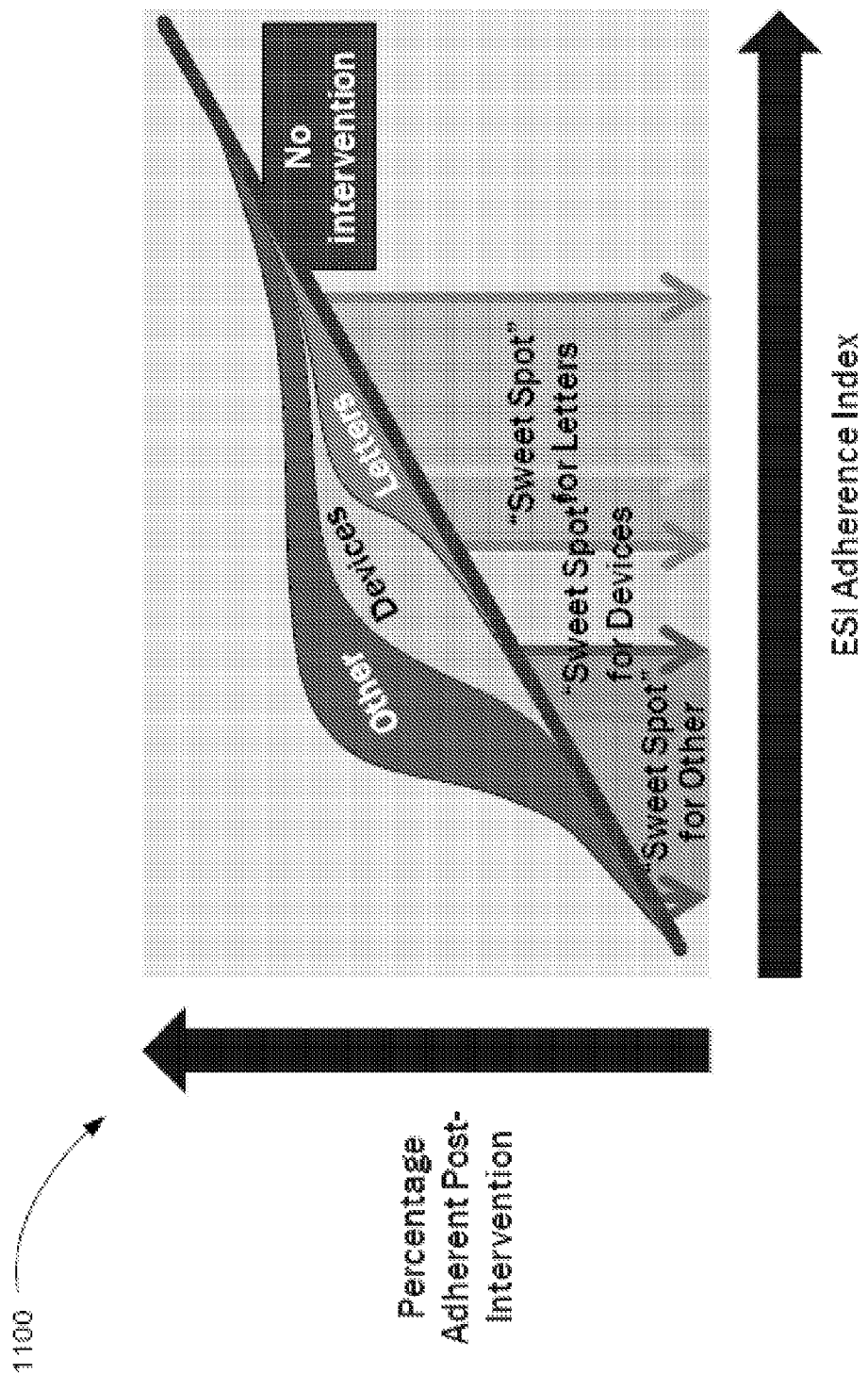

FIG. 11 is an example chart 1100, according to an example embodiment. The chart 1100 indicates the percentage adherent post intervention. The chart 1100 reflects a "sweet spot" were a particular type of intervention may have a higher degree of effectiveness than other segments of the population.

Figure 12:
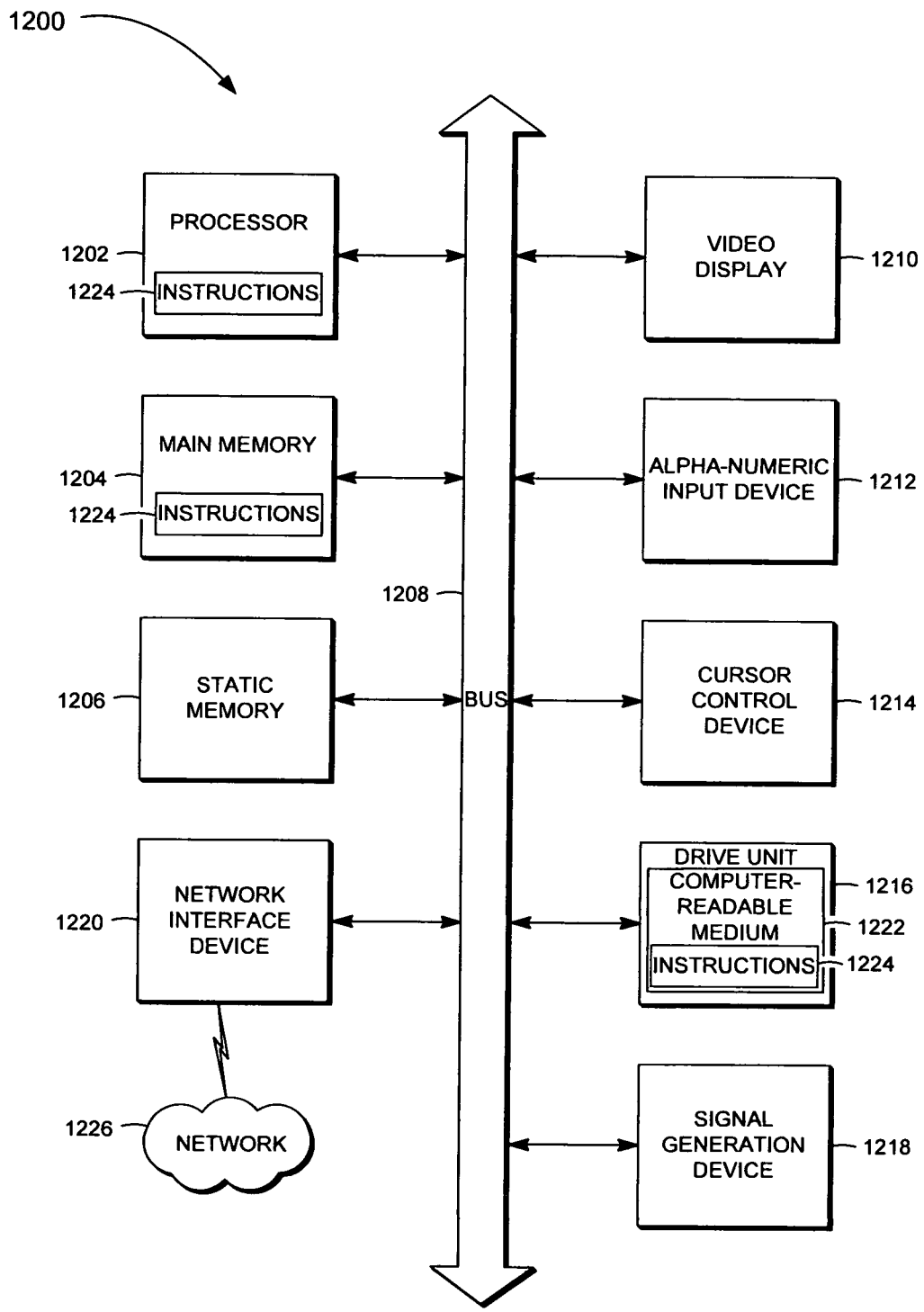
FIG. 12 is a block diagram of a machine in the example form of a computer system within which a set of instructions for causing the machine to perform any one or more of the methodologies discussed herein may be executed.

FIG. 12 shows a block diagram of a machine in the example form of a computer system 1200 within which a set of instructions may be executed causing the machine to perform any one or more of the methods, processes, operations, or methodologies discussed herein. The program selection device 102, the consultant communication device 106, and/or the adherence prediction device 108 may include the functionality of the one or more computer systems 1200.

In an example embodiment, the machine operates as a standalone device or may be connected (e.g., networked) to other machines In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1200 includes a processor 1212 (e.g., a central processing unit (CPU) a graphics processing unit (GPU) or both), a main memory 1204 and a static memory 1206, which communicate with each other via a bus 1208. The computer system 1200 may further include a video display unit 1120 (e.g., a liquid crystal display (LCD) or a cathode ray tube (CRT)). The computer system 1200 also includes an alphanumeric input device 1212 (e.g., a keyboard), a cursor control device 1214 (e.g., a mouse), a drive unit 1216, a signal generation device 1218 (e.g., a speaker) and a network interface device 1220.

The drive unit 1216 includes a computer-readable medium 1222 on which is stored one or more sets of instructions (e.g., software 1224) embodying any one or more of the methodologies or functions described herein. The software 1224 may also reside, completely or at least partially, within the main memory 1204 and/or within the processor 1212 during execution thereof by the computer system 1200, the main memory 1204 and the processor 1212 also constituting computer-readable media.

The software 1224 may further be transmitted or received over a network 1226 via the network interface device 1220. While the computer-readable medium 1222 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media.

Figure 13A:
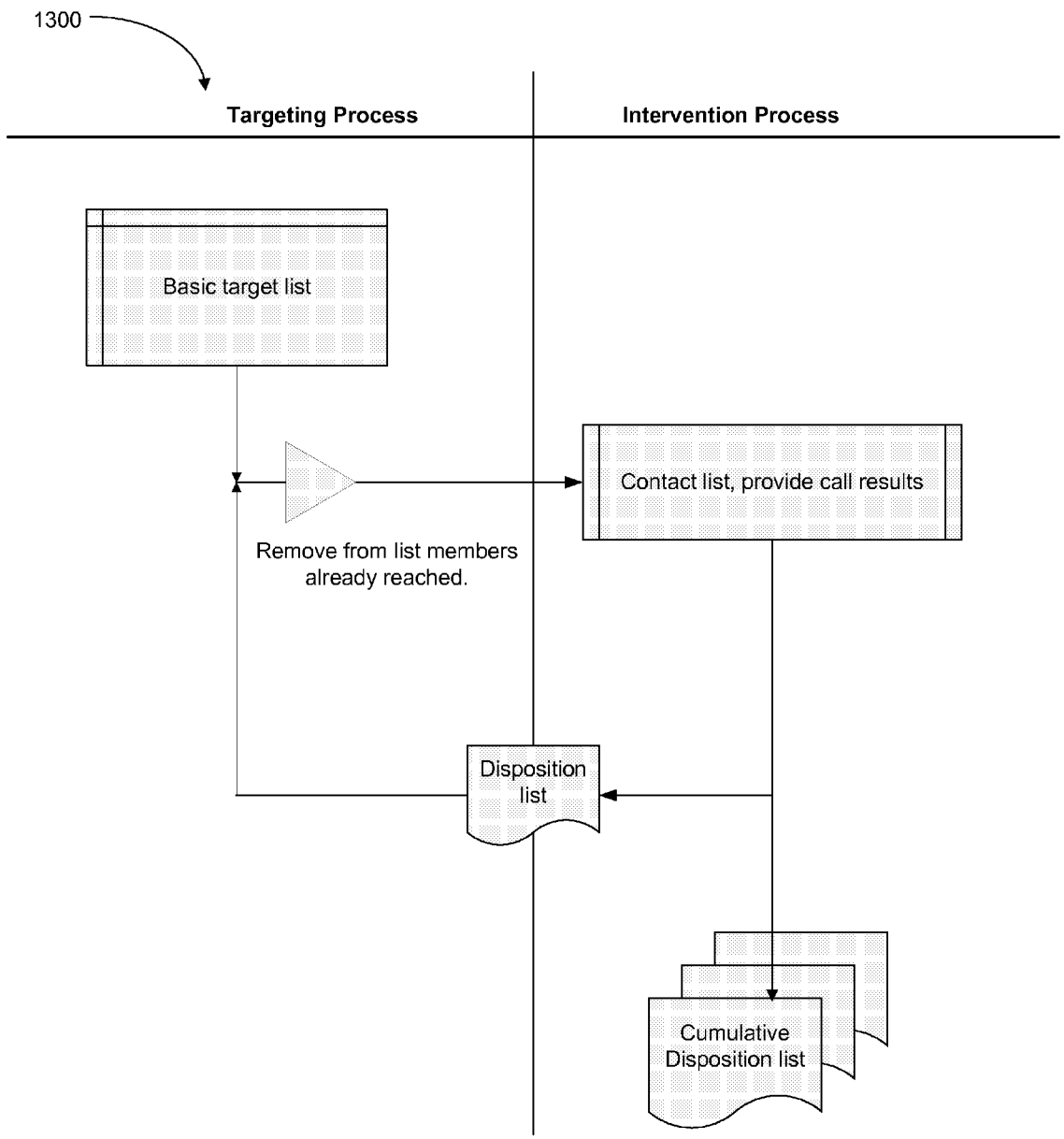
FIGS. 13A, 13B and 13C are a block diagram of the top level process flow, according to an example embodiment.
Figure 13B:
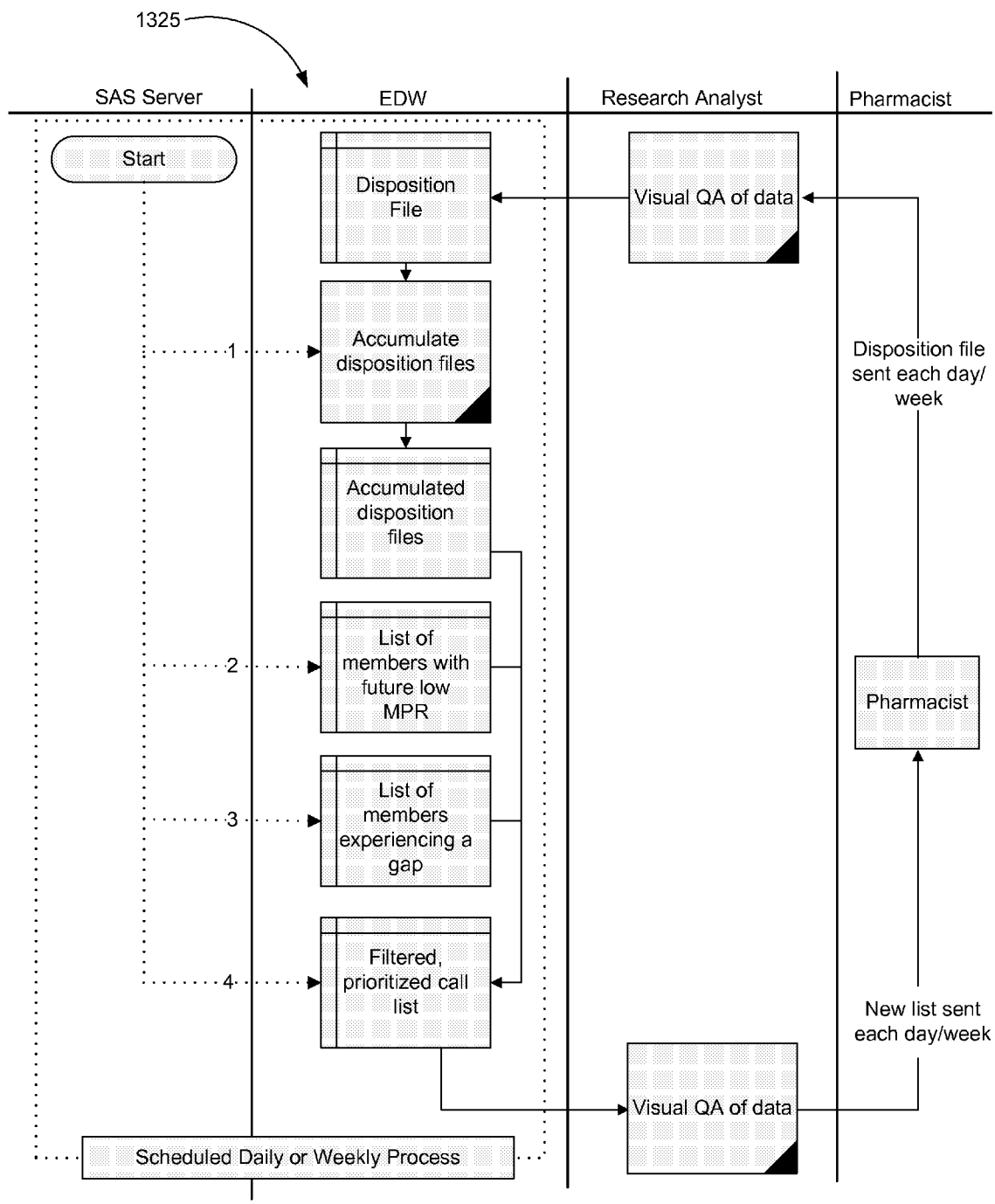
Figure 13C:
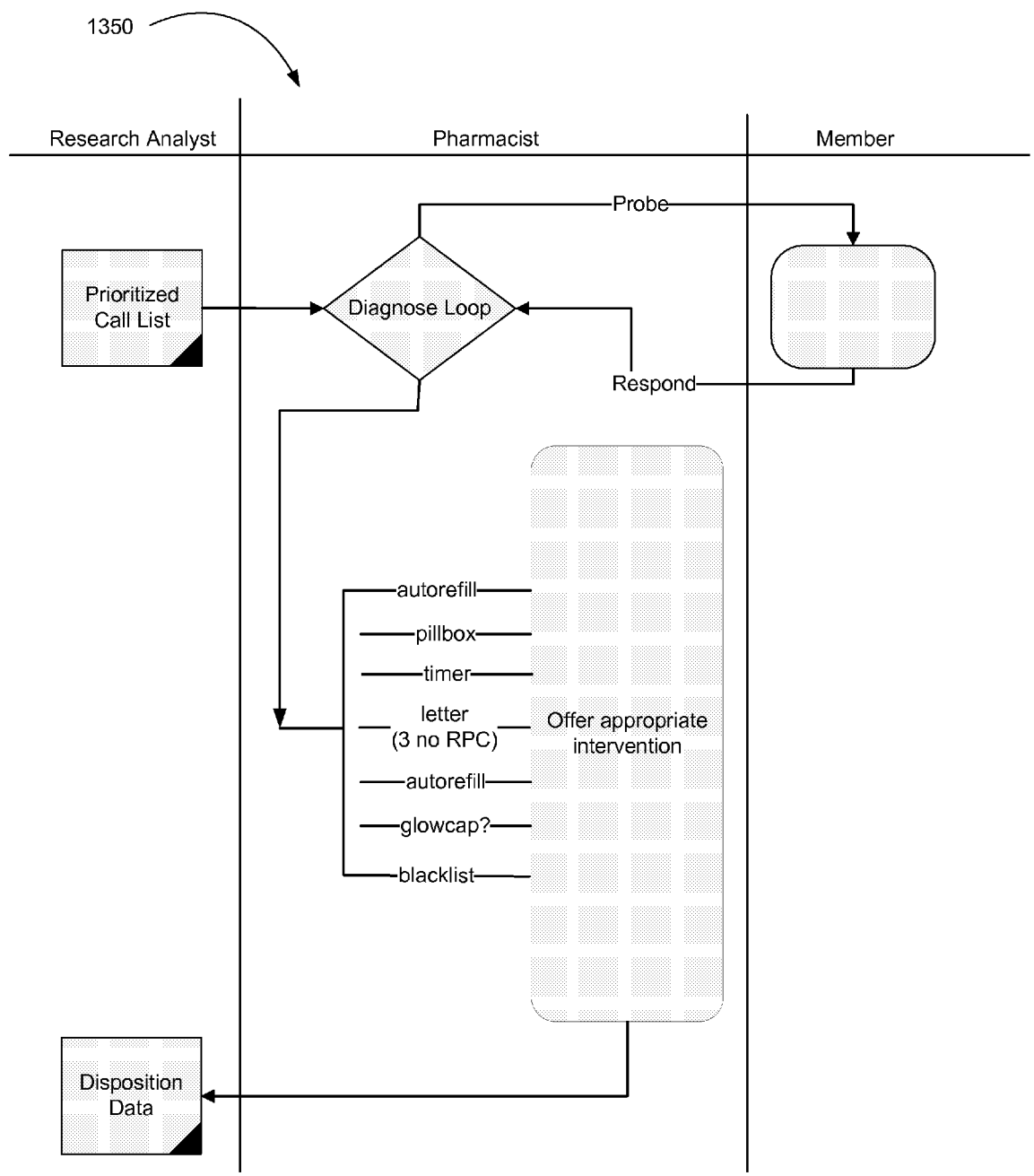
Figure 14A:
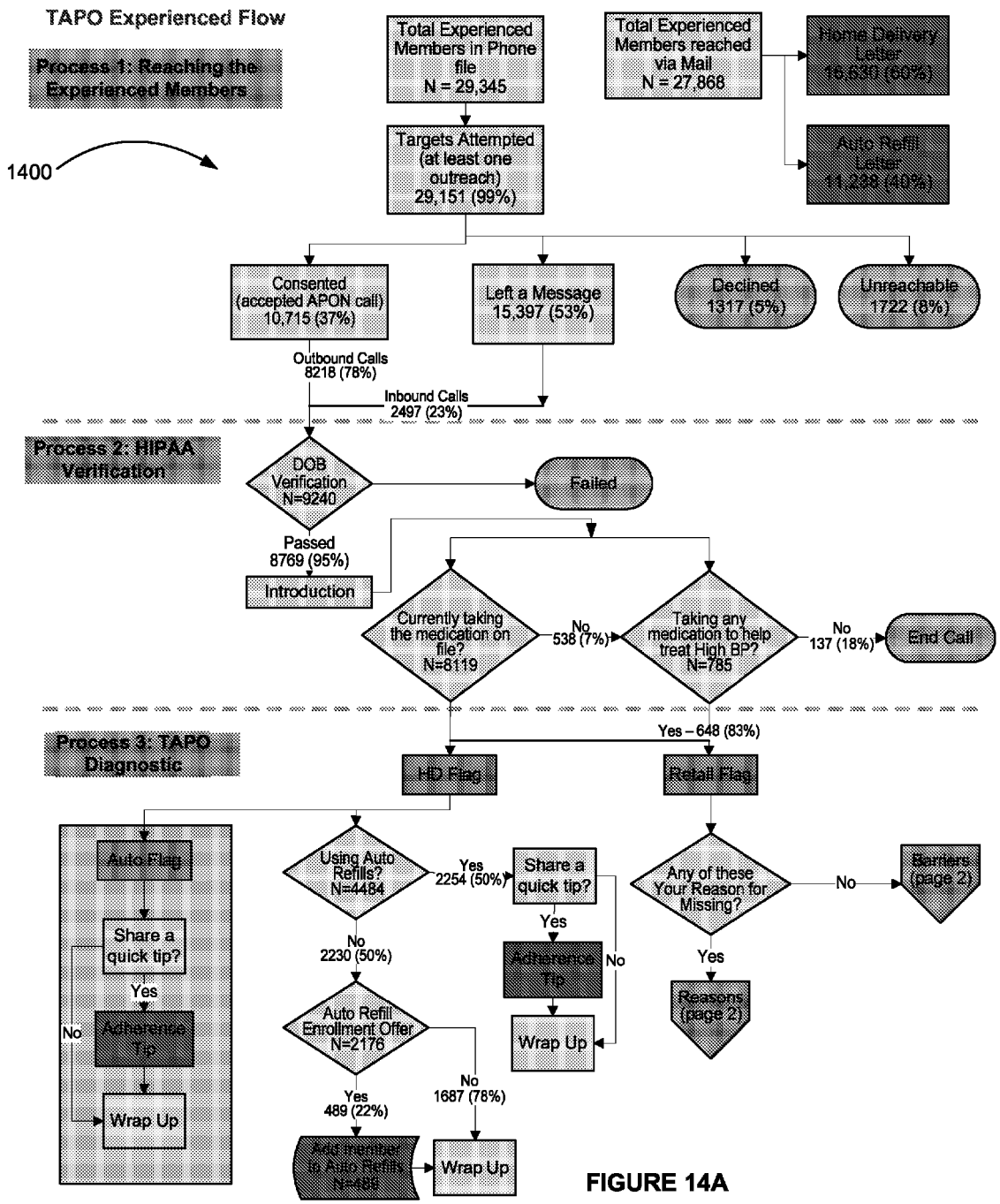
Figures 1, 14B:
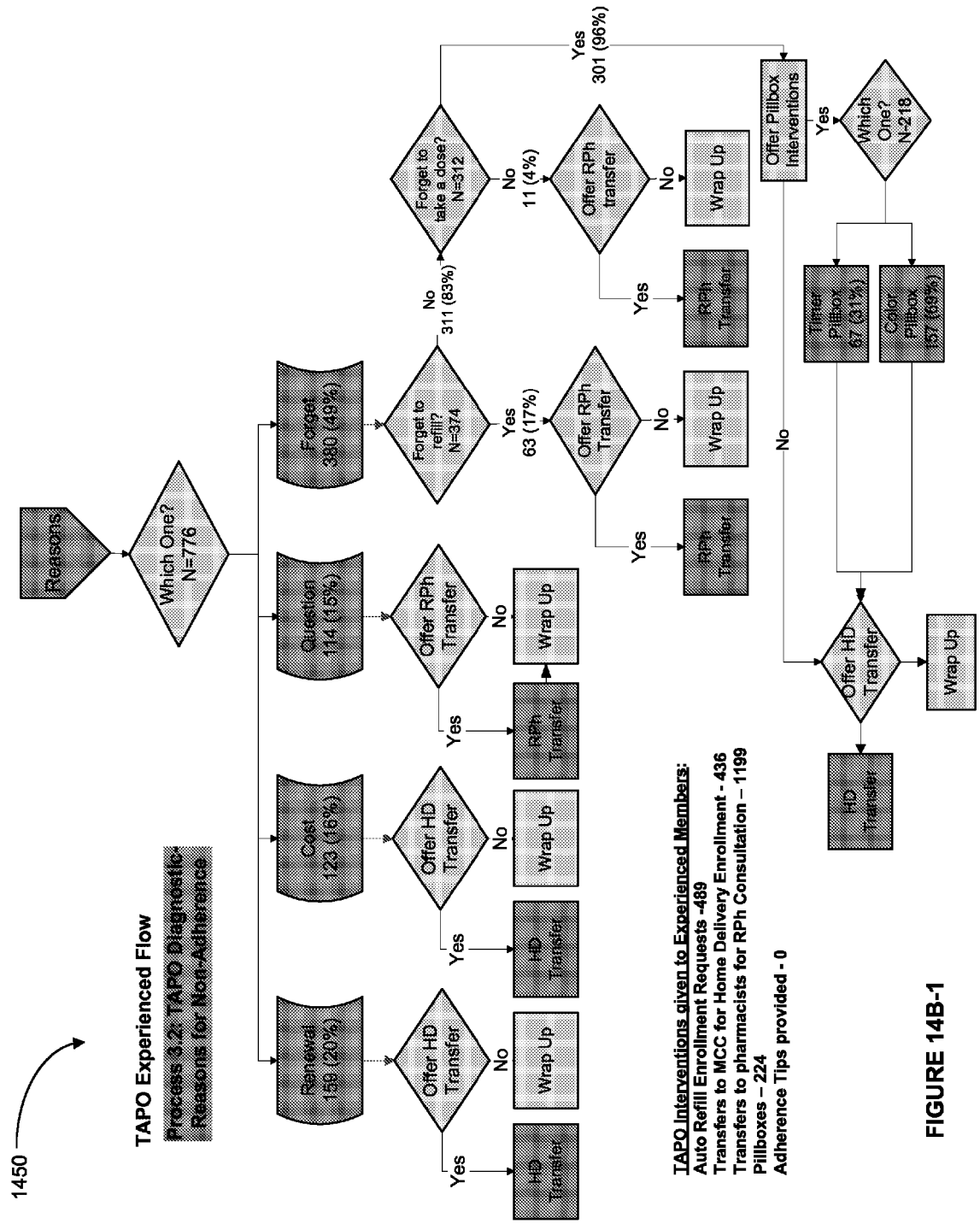
Figures 2, 14B:
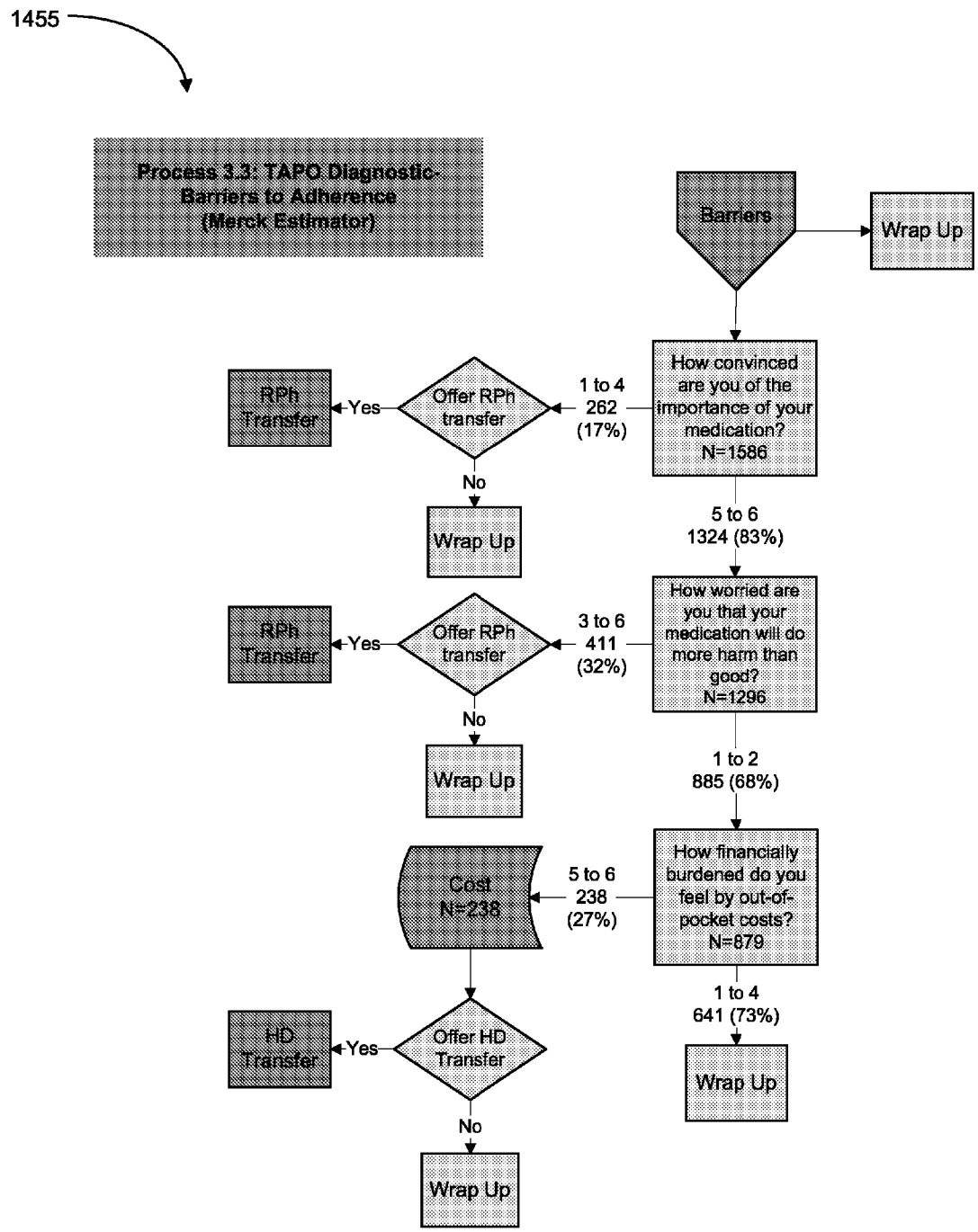

Referring to FIGS. 13A, 13B and 13C, a block diagram of the top level process flow is shown. The targeting process utilizes a basic member target list of those members who have been identified by the model as those who have not met a predefined adherence threshold. As members are contacted through the intervention process and program implementation has been identified, the contacted members may be added to a disposition list and the members may be removed from the basic target list. A cumulative disposition list may also be maintained over time. Continuously or periodically the disposition files may be accumulated and previously contacted members may be tracked to determine their adherence behavior. Based on the behavior found, a list of members having a low MPR may be determined and from that list a priority list may be filtered by the likelihood of success to improve adherence. During this tracking and evaluation process, the data may also be visually examined by research analyst and other experts like pharmacists. This may be used as a sanity check to make sure that the predictions and data patterns that are detected add up in a logical manner. Expert consultants may also communicate with members in a manner designed to improve member adherence to therapy.

Figure 15A:
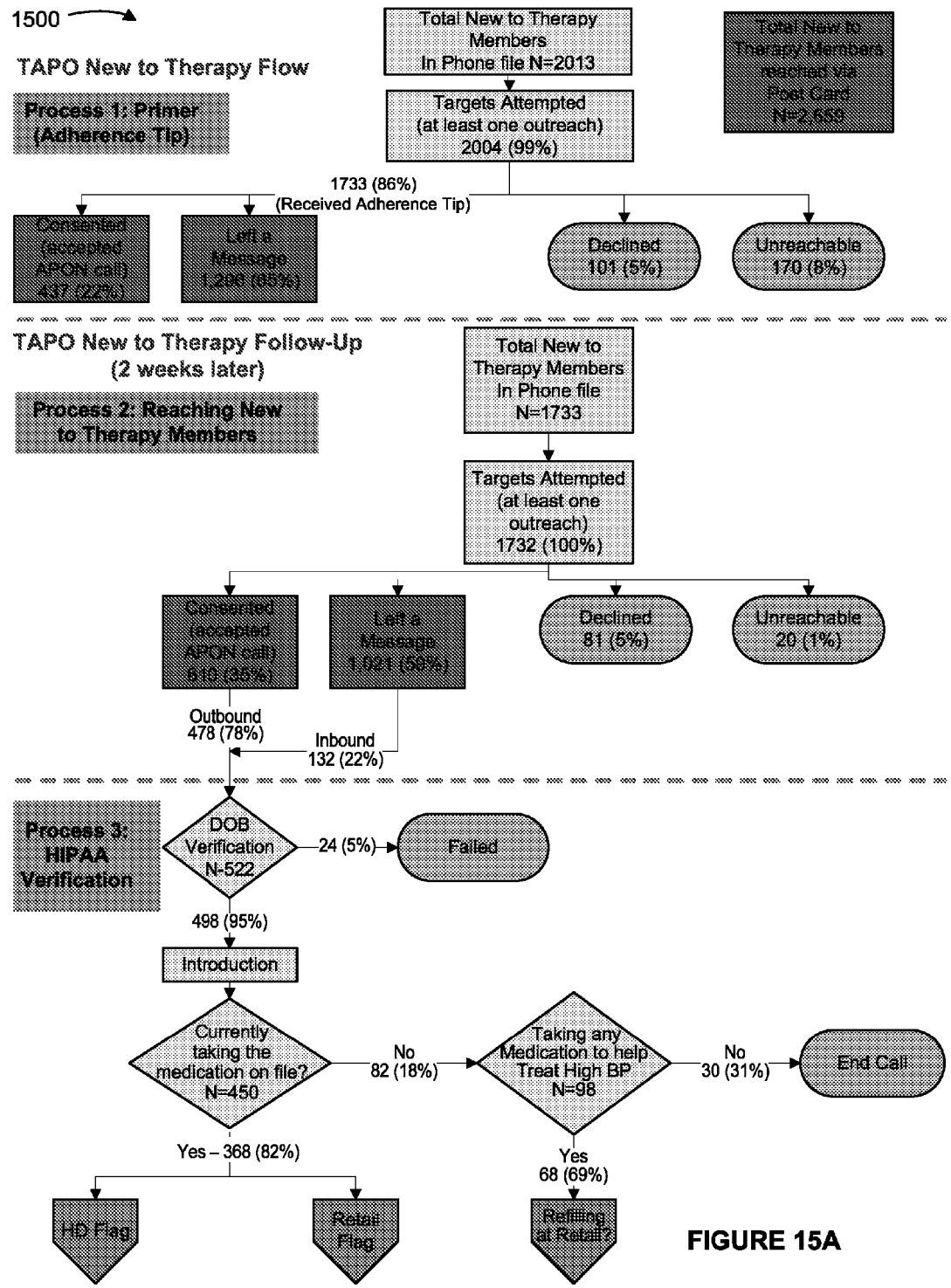
FIGS. 15A and 15B are a block diagram of the TAPO Experience flow for a new member, according to an example embodiment.
Figure 15B:
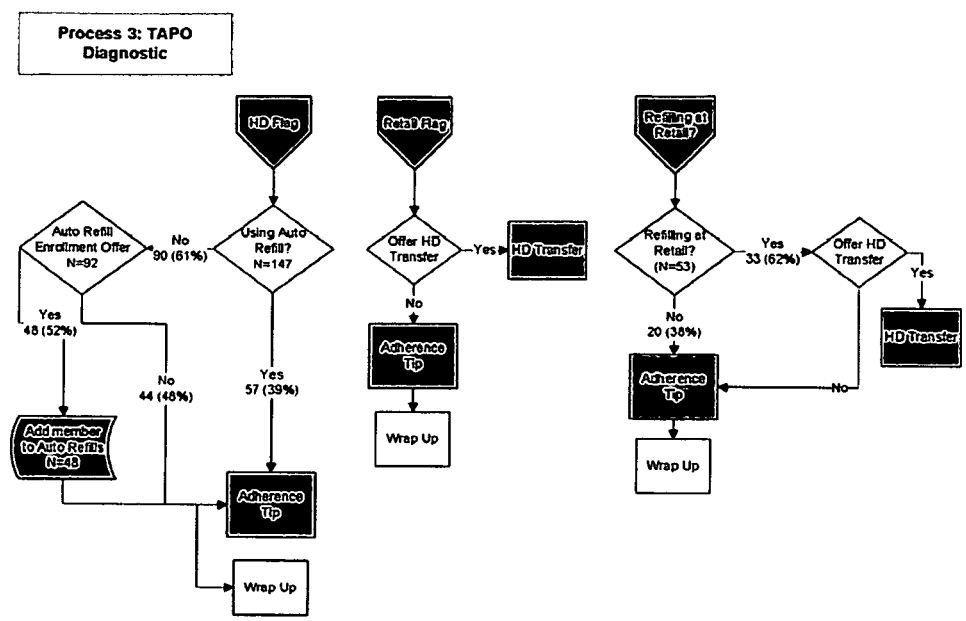
Figure 16A:
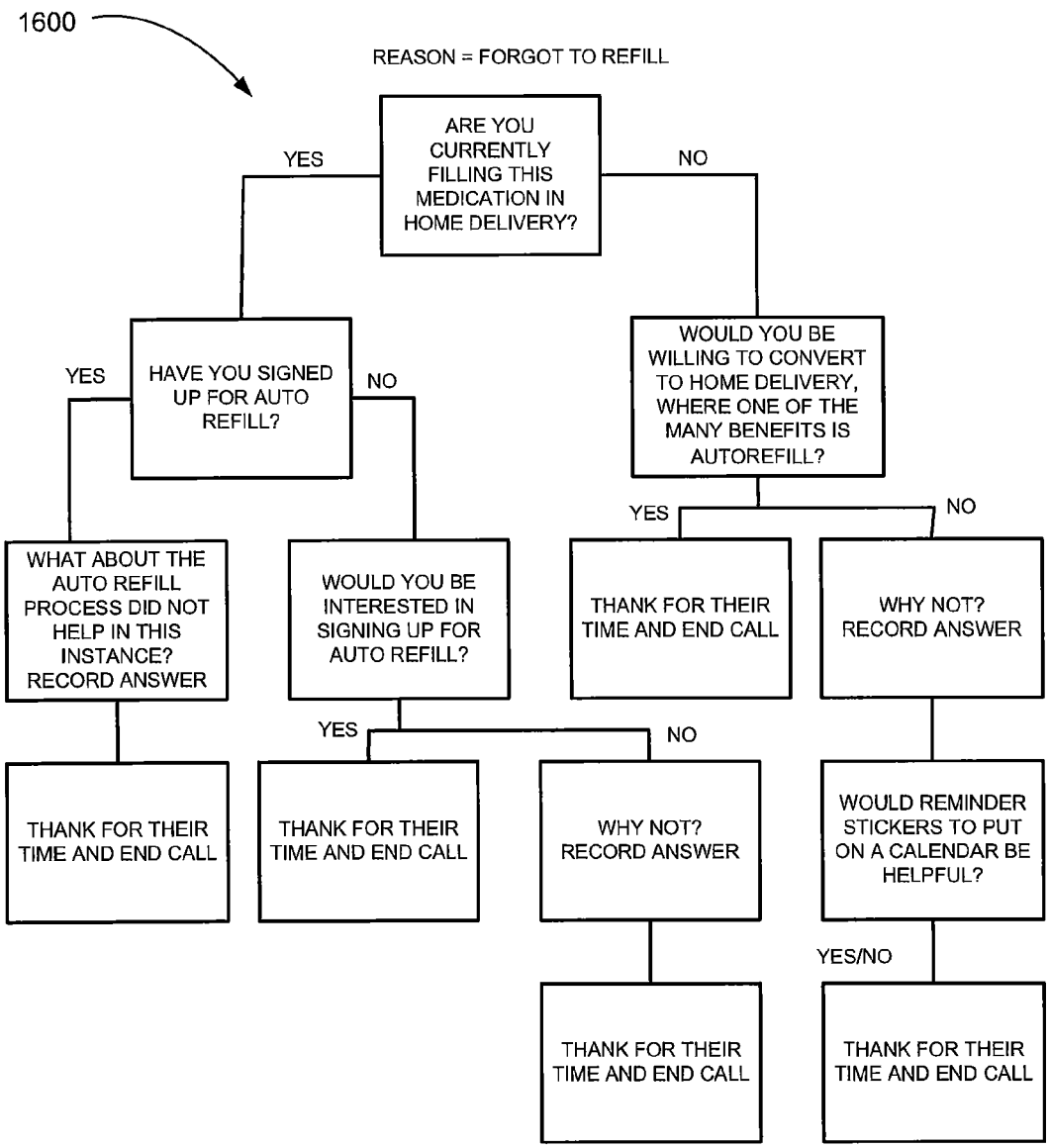
FIGS. 16A, 16B, 16C, 16D and 16E are a block diagram of a basic script for the TAPO Experience, according to an example embodiment.
Figure 16B:
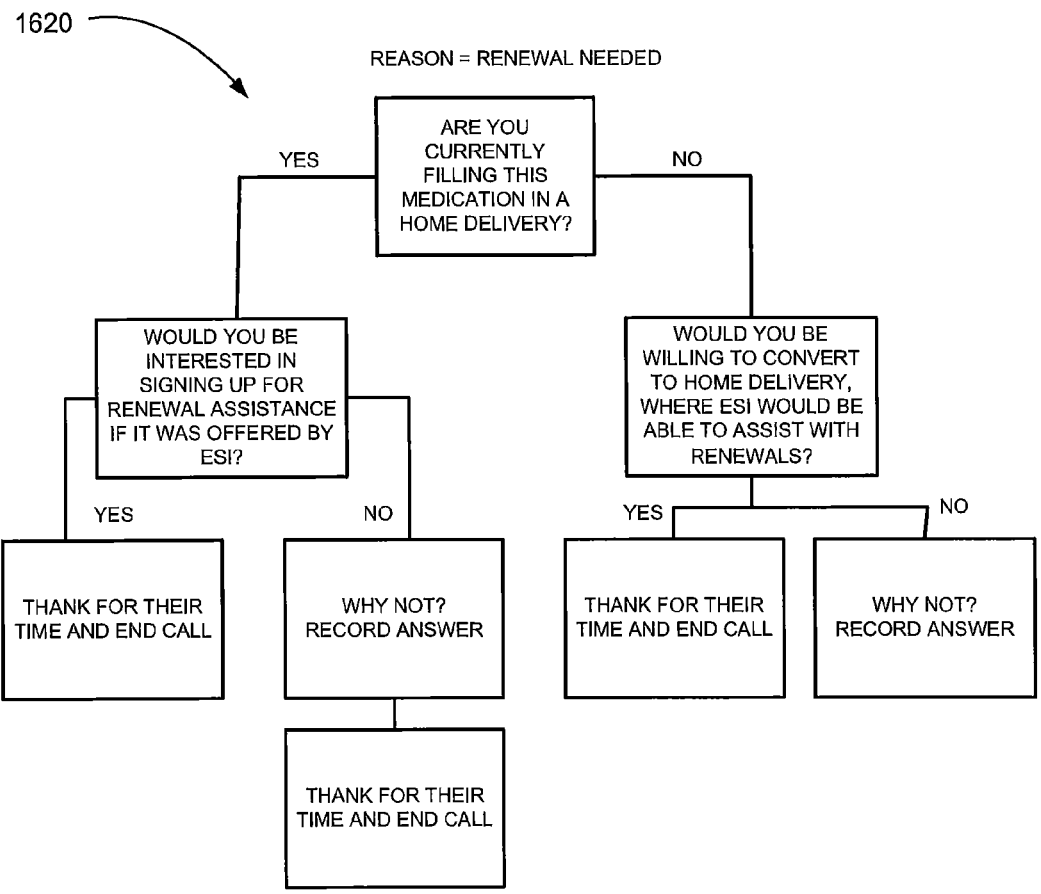
Figure 16C:
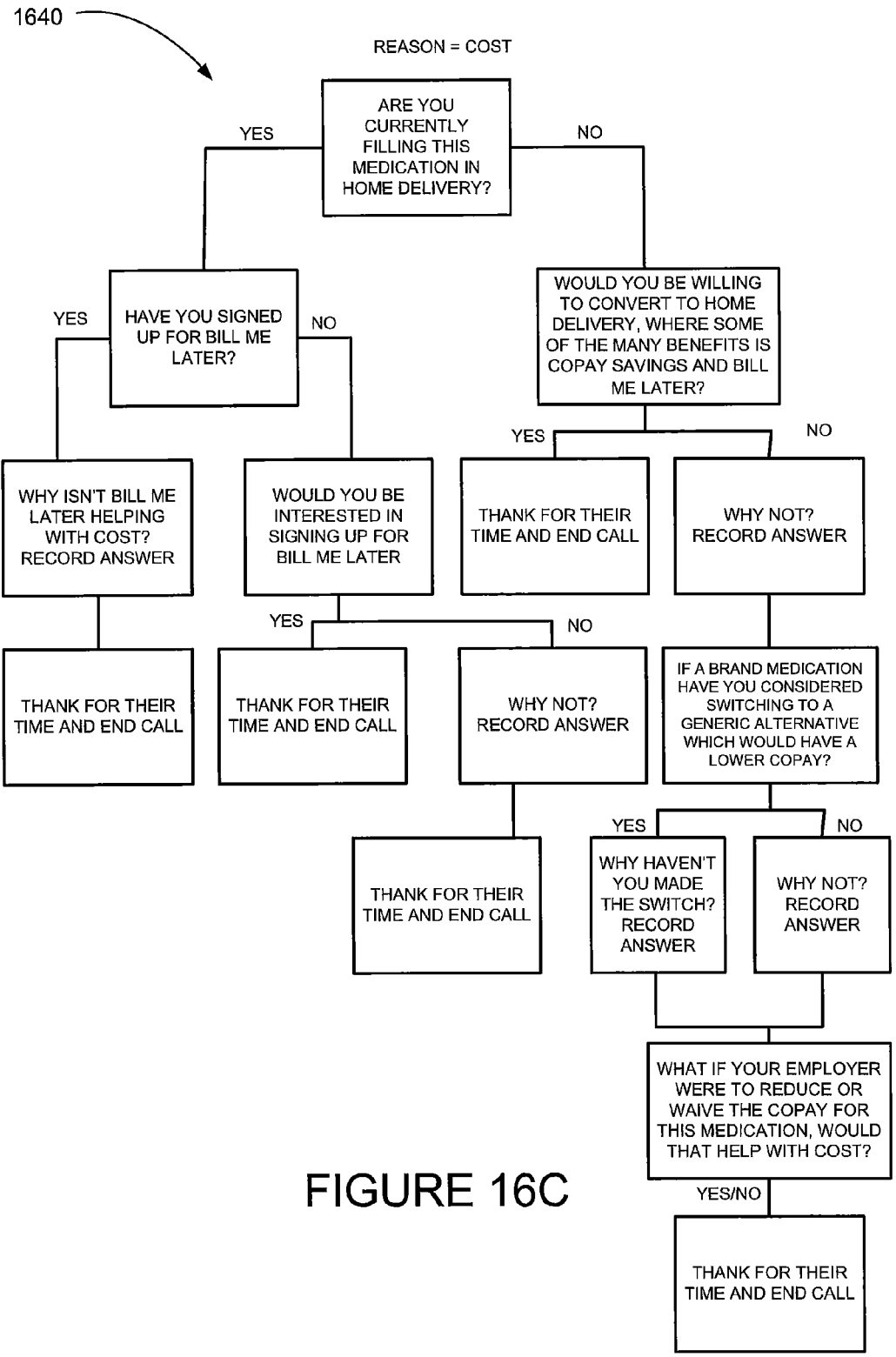
Figure 16D:
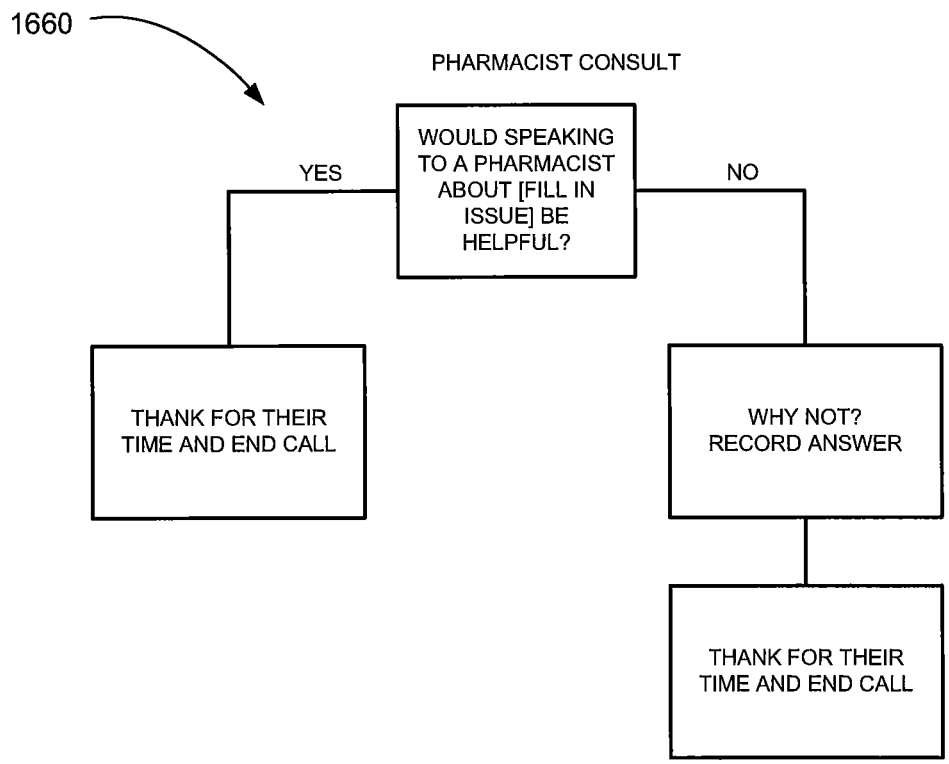
Figure 16E:
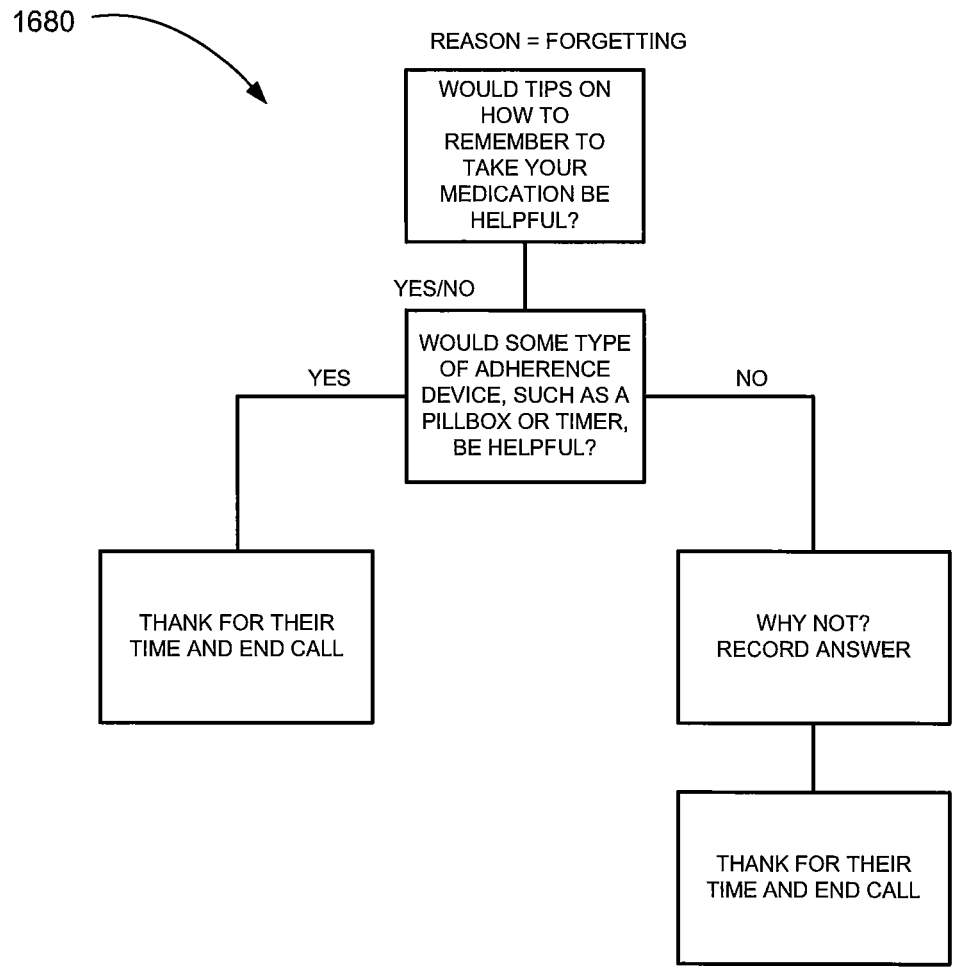

Referring to FIGS. 14A, 14B-1, 14B-2, 15A and 15B, a block diagram of an example TAPO (Therapy Adherence Proactive Outreach) experience flow for an experienced member and for a new member is shown. The model may predict at-risk patients that will have a greater likelihood of not adhering to drug therapy and may be targeted for an outreach contact and the likely barrier to adherence can also be determined and intervention at the individual member level should be accomplished. The predictive modeling is a driver for TAPO to determine what intervention is decided. FIGS. 14A, 14B-1, and 14B-2 illustrate the TAPO flow for an experienced member and FIGS. 15A and 15B is for a new member.

An outreach may be attempted with the experienced member. A letter may be sent offering home delivery and auto refill. Telephone calls may also be attempted. If a member is reached by telephone, certain demographic questions may be asked of the member to obtain more specific individual demographics. A diagnostic may also be performed after certain inquiries are posed to the member. If poor adherence is determined, reasons for lack of adherence may be sought. A diagnostic may be performed to determine the barriers to adherence. Interventions may be determined based on the information gathered from the member. A similar process is provided for a new member.

Referring to FIGS. 16A, 16B, 16C, 16D and 16E, a block diagram of a basic script for the TAPO experience is shown. The flow diagrams show a representative TAPO script for various different reasons for non-adherence and how a communicative intervention with a patient may attempt to get the patient back on track. In one representative script, during the intervention with the patient, an auto refill offering is made. Another is representative of a script were the underlying reason is a renewal for a maintenance medication is overdue and a home delivery program offering is made to the patient. Another script is representative where the cost of the medication is the issue and home delivery is offered to bring down the cost and another alternative is offered as a bill me later program alternative. A pharmacist consultant contact is also represented and a scenario where forgetting is the reason for non-adherence and various reminder devices are offered to the patient as a potential program to improve patient adherence.

Figure 17:
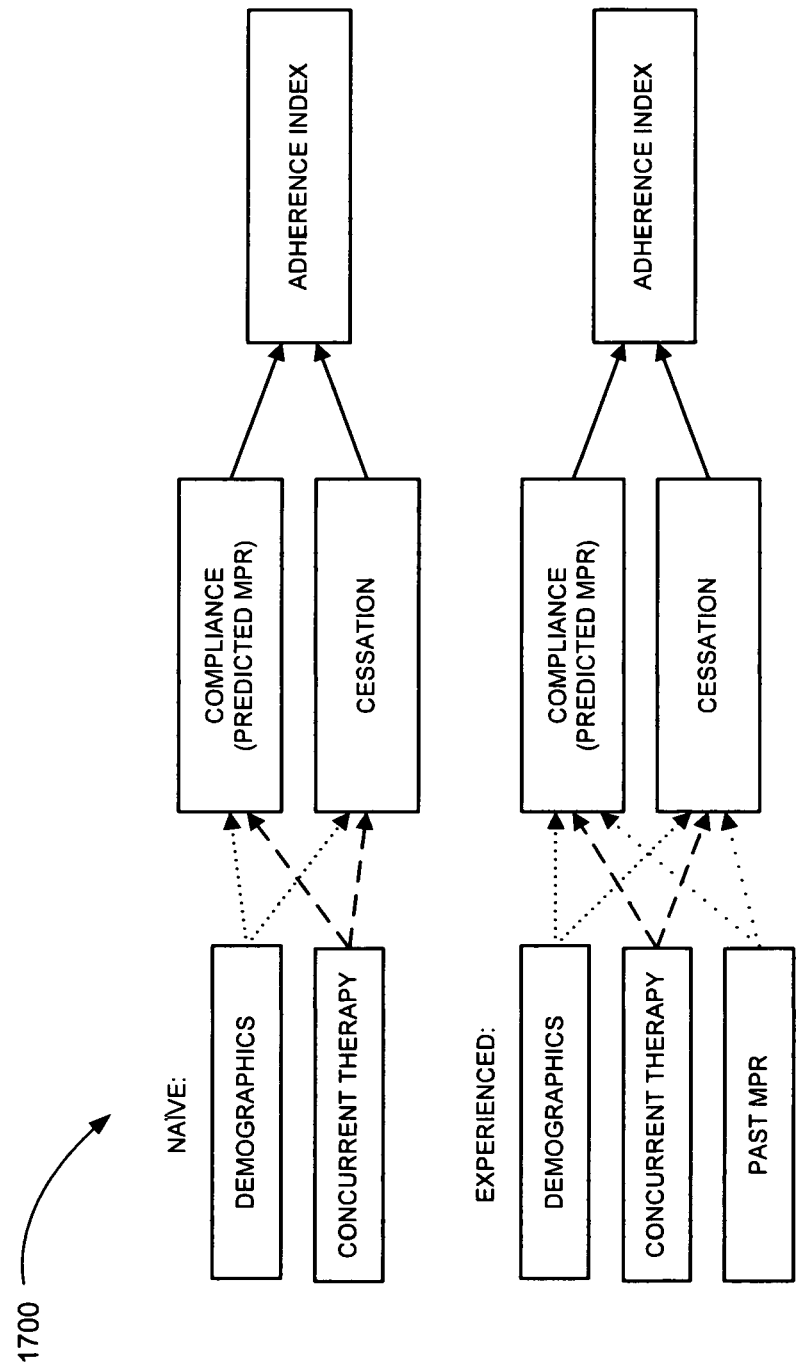
FIG. 17 is a block diagram of an adherence model, according to an example embodiment.

Referring to FIG. 17, as discussed herein the adherence prediction model can be separated into two components, a naive (new) member component and an experienced (continuous) member component. Each of the components can perform a statistical analysis of the demographic data and concurrent therapy data. Further, each component of the module can include a compliance module and a cessation module. In either case, a predicted MPR can be calculated based on the demographics. The predicted MPR can be factored in to refine the compliance module. Once actual demographic and actual past MPR data has been gathered and actual past MPR can be factored in with the demographics and concurrent therapy in the case of the experienced member component. As more and more data is gathered, this actual past MPR factor can continue to refine the model. Further, as actual data is gathered a future MPR can be predicted and potentially utilized to factor in with the compliance module.

Therefore, there can be four underlying models and they are the new member predicted MPR refined compliance model, the new member cessation model, the experienced member predicted MPR refined compliance model and the experience member cessation model. These underlying models can be further refined based on type of disease or type of medication therapy and the associated behavioral data, which may correlate to a particular set of characteristics for why people may not be adherent. For example, behavior data may reflect what appears to be a totally obscure factor that appears to have nothing to do with the disease state, but shows up as a statistically significant event and is repeatable and can be validated. The present invention can also factor in this statistically significant event. Further, the validation of the model and the statistically significant event is a continuous refinement. The model can capture patterns of behavior that may be related to disease type or medication therapy or other factor and can extract things that are common. If a pattern is identified as statistically significant, then that is one of the factors used for the prediction of future compliance.

In an example embodiment, a member is targeted a based on an adherence index calculation. The targeted member can be contacted via a member interface and prompted with a humanly interpretable communication, which can include demographic questions, drug therapy questions, lack of adherence questions and offerings of alternative new programs to assist in adherence. The member may respond to the prompt and the response may be run through a diagnostic model and real time adherence tips can be communicated to the member via the member interface with humanly interpretable tip communications. Demographic response data from the member, drug therapy response data and lack of adherence response data may be stored in a database.

Future member adherence behavior while under new program offering may be tracked if member affirmatively responds and accepts the alternative program offering. The future member behavior may be captured and stored in a database. A consultant may be contacted via a consultant interface and the consultant may be prompted with a humanly interpretable communication, which requests the consultant send a member adherence assistance communication to the member via member interface.

Another example embodiment includes a system having a drug therapy prediction computing system having a prediction processor function. Within the computing system, a processor executable adherence prediction module can reside and a processor executable medication possession ratio module may reside both of which can be executed by the processor function of the computing system. The adherence prediction module when executed by the processor may calculate the adherence index and the medication possession ratio module when executed by the processor function may calculate the MPR. The system may also include a database server subsystem having a data server function, which includes computer readable memory that can be accessed. The database memory may have stored thereon, accessible historical demographic data and related probability factors. A program selection computing subsystem may have a selection processor function and a processor executable program selection module. The drug therapy prediction computing subsystem, demographic database server subsystem and the program selection computing subsystem may be communicably linked over a system network. The prediction processor function may be operable to retrieve demographic data and probability factors and further operable to execute the adherence prediction module to calculate an adherence index and further operable to execute the medication possession ration module to calculate a predicted MPR based on said demographic data and related probability factors. The module may further factor in the MPR with the adherence index calculation to calculate likelihood of adherence. The selection processor function may be operable to retrieve demographic data and related probability factors and execute the program selection module to select a program to address member adherence. The adherence prediction module may also include a cessation prediction module and a compliance prediction module to segregate these two components.

This example embodiment may also include a consultant communication computing subsystem having a consultant communication processor function and a consultant communication user interface module where the consultant communication processor may be operable to execute the consultant communication user interface module to receive and transmit consultant adherence assistance communications. A patient communication computing subsystem may be part of the system, which has a patient communication processor function and a patient communication user interface module where the patient communication processor may be operable to execute the patient communication user interface module to receive and transmit patient adherence assistance communications.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled. The inventive subject matter may be represented in a variety of different embodiments of which there are many possible permutations.

Thus, methods and systems for improving therapy adherence have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
accessing, on a processor, claims data associated with a patient;
determining, on the processor, whether the patient is new to therapy or is continuing therapy relative to a drug therapy program for a prescription drug;
selecting, on the processor, a cessation predictive model and a compliance predictive model among a plurality of available predictive models based on a determination of whether the patient is new to therapy or is continuing therapy;
utilizing the cessation predictive model and the claims data to calculate, on the processor, a likelihood of the patient to continue the drug therapy program for the prescription drug;
utilizing the compliance predictive model and the claims data to calculate, on the processor, a likelihood of the patient to comply with the drug therapy program for the prescription drug;
calculating, on the processor, a likelihood of patient adherence of the patient with the prescription drug based on the likelihood of the patient to continue the drug therapy program and the likelihood of the patient to comply with the drug therapy program;

determining, on the processor, where in an adherence range the likelihood of patient adherence falls; and selecting, on the processor, a therapy adherence program likely to increase therapy adherence for the patient based on a determination of a location within a mid-portion of the adherence range.

2. The method of claim 1, further comprising:

determining a disease state associated with the patient, wherein selection of the cessation predictive model and the compliance predictive model is based on the determination of whether the patient is new to therapy or is continuing therapy and a determination of the disease state.

3. The method of claim 1, further comprising:

measuring the medication possession ratio (MPR) of the patient, wherein determining where in the adherence range the likelihood of patient adherence falls includes determining where in the adherence range based on the MPR of the patient and the likelihood of patient adherence.

4. The method of claim 1, further comprising:

generating the compliance predictive model, the cessation predictive model, or both the compliance predictive model and the cessation predictive model based on an age factor, an income factor, a disease severity factor, a number of medications factor, a symptomatic disease factor, a partner status factor, and a partner adherent to maintenance medications factor associated with a patient population.

5. The method of claim 1, further comprising:

generating the compliance predictive model, the cessation predictive model, or both the compliance predictive model and the cessation predictive model includes utilizing variable clustering on population claims data associated with a plurality of patients, selection of candidate variables based on a result of the variable clustering, and performance of bivariate screening on selected candidate variables to select a final variable set for the compliance predictive model, the cessation predictive model, or both the compliance predictive model and the cessation predictive model.

6. The method of claim 1, wherein the therapy adherence program includes an intervention.

7. The method of claim 6, wherein the intervention includes a letter communication, use of prescription drug home delivery, use of a specialty pharmacy for delivery of the prescription drug, a patient notification device, a co-pay reduction, or combinations thereof.

8. The method of claim 1, wherein the therapy adherence program includes a window of time in which to implement the intervention.

9. The method of claim 1, wherein utilizing the cessation predictive model and the claims data to calculate comprises utilizing the cessation predictive model, the claims data, and demographics data associated with the patient to calculate the likelihood of the patient to continue the drug therapy program for the prescription drug, and wherein utilizing the compliance predictive model and the claims data to calculate comprises utilizing the compliance predictive model, the claims data, and demographic data to calculate the likelihood of the patient to comply with the drug therapy program for the prescription drug.

10. The method of claim 1, further comprising:

determining a primary non-adherence cause associated with the patient, wherein selection of the therapy adherence program likely to increase therapy adherence for the patient is based on the location within the mid-portion of the adherence range and the primary non-adherence cause associated with the patient.

11. The method of claim 1, further comprising:

identifying the patient among a plurality of patients based on a known or predicted health condition associated with the patient.

12. The method of claim 1, further comprising:

calculating the medication possession ratio (MPR) and a refill gap delay for a plurality of patients; and selecting the patient among a plurality of patients based on calculation of the MPR and the refill gap delay.

13. The method of claim 1, wherein calculation of the likelihood of patient adherence is made prior to the patient having a gap in a prescription refill of the prescription drug, prior to have a gap in care, or prior to having a gap in a prescription refill and a gap in care.

14. The method of claim 1, further comprising:

generating a patient therapy offer communication based on selection of the therapy adherence program; and transmitting the patient therapy offer communication.

15. The method of claim 14, further comprising:

receiving a patient therapy response communication in response to transmission of the patient therapy offer communication; and enrolling the patient in a home delivery program in response to receipt of the patient therapy response communication.

16. A non-transitory machine readable medium comprising machine executable instructions, where when executed by one or more processors causes the one or more processors to perform the following instructions:

access claims data associated with a patient;

determine whether the patient is new to therapy or is continuing therapy relative to a drug therapy program for a prescription drug;

select a cessation predictive model and a compliance predictive model among a plurality of available predictive models based on a determination of whether the patient is new to therapy or is continuing therapy;

utilize the cessation predictive model and the claims data to calculate, on the processor, a likelihood of the patient to continue a drug therapy program for a prescription drug;

utilize the compliance predictive model and the claims data to calculate, on the processor, a likelihood of the patient to comply with the drug therapy program for the prescription drug;

calculate a likelihood of patient adherence of the patient based on the likelihood of the patient to continue the drug therapy program and the likelihood of the patient to comply with the drug therapy program;

determine where in an adherence range the likelihood of patient adherence falls; and select a therapy adherence program likely to increase therapy adherence for the patient based on a determination of a location within a mid-portion of the adherence range.

* * * * *